United States Patent
Offutt et al.

(10) Patent No.: US 12,076,564 B2
(45) Date of Patent: Sep. 3, 2024

(54) PATIENT SPECIFIC OPTIMIZATION ALGORITHM

(71) Applicant: Medtronic, Inc., Minneapolis, MN (US)

(72) Inventors: Sarah J. Offutt, Golden Valley, MN (US); Katie C. Bittner, White Bear Lake, MN (US); Lisa M. Jungbauer Nikolas, Lino Lakes, MN (US); Juan G. Hincapie, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 558 days.

(21) Appl. No.: 17/215,685

(22) Filed: Mar. 29, 2021

(65) Prior Publication Data
US 2021/0316145 A1 Oct. 14, 2021

Related U.S. Application Data
(60) Provisional application No. 63/009,710, filed on Apr. 14, 2020.

(51) Int. Cl.
*A61N 1/36* (2006.01)

(52) U.S. Cl.
CPC ..... *A61N 1/36135* (2013.01); *A61N 1/36189* (2013.01)

(58) Field of Classification Search
CPC .......... A61N 1/36135; A61N 1/36189
See application file for complete search history.

(56) References Cited

U.S. PATENT DOCUMENTS

| 6,463,328 B1 | 10/2002 | John |
| 7,305,268 B2 | 12/2007 | Gliner et al. |
| 7,369,894 B2 | 5/2008 | Gerber |
| 7,801,618 B2 | 9/2010 | Pless |

(Continued)

FOREIGN PATENT DOCUMENTS

| EP | 3473294 A1 | 4/2019 |
| WO | 2000/01320 A2 | 1/2000 |

(Continued)

OTHER PUBLICATIONS

International Preliminary Report on Patentability from International Application No. PCT/US2021/026415 dated Oct. 27, 2022, 9 pp.

(Continued)

*Primary Examiner* — Joseph M Dietrich
(74) *Attorney, Agent, or Firm* — Shumaker & Sieffert, P.A.

(57) ABSTRACT

A system may receive first information relating to a patient captured during a baseline period that is prior to the patient receiving stimulation. The system may receive second information relating to the patient captured during an initial therapy assignment. The second information may include testing data generated by delivering stimulation during an implant procedure. The system may determine initial stimulation program settings based on the first information, the second information and population-informed information. The population-informed information may be related to other patients. The system may cause, during a training period, delivery of therapy based on the initial stimulation program settings.

23 Claims, 8 Drawing Sheets

(56) References Cited

U.S. PATENT DOCUMENTS

| | | | |
|---|---|---|---|
| 7,853,323 | B2 | 12/2010 | Goetz |
| 8,204,597 | B2 | 6/2012 | Gerber et al. |
| 8,554,331 | B2 | 10/2013 | Gerber et al. |
| 8,615,299 | B2 | 12/2013 | Goetz |
| 8,702,629 | B2 | 4/2014 | Giuffrida et al. |
| 8,731,656 | B2 | 5/2014 | Bourget et al. |
| 8,792,991 | B2 | 7/2014 | Gerber et al. |
| 8,805,508 | B2 | 8/2014 | Gerber et al. |
| 8,874,217 | B2 | 10/2014 | Alataris et al. |
| 8,989,861 | B2 | 3/2015 | Su et al. |
| 9,272,140 | B2 | 3/2016 | Gerber |
| 9,555,246 | B2 | 1/2017 | Jiang et al. |
| 9,561,372 | B2 | 2/2017 | Jiang et al. |
| 9,592,004 | B2 | 3/2017 | DiLorenzo et al. |
| 9,649,439 | B2 | 5/2017 | John |
| 9,669,219 | B2 | 6/2017 | Caparso et al. |
| 9,956,404 | B2 | 5/2018 | Brink et al. |
| 9,959,388 | B2 | 5/2018 | Grandhe et al. |
| 10,004,901 | B2 | 6/2018 | Gliner |
| 10,029,102 | B2 | 7/2018 | Doan et al. |
| 10,076,667 | B2 | 9/2018 | Kaula et al. |
| 10,118,037 | B2 | 11/2018 | Kaula et al. |
| 10,124,171 | B2 | 11/2018 | Kaula et al. |
| 10,265,532 | B2 | 4/2019 | Carcieri et al. |
| 10,272,247 | B2 | 4/2019 | Bokil et al. |
| 10,299,987 | B2 | 5/2019 | Greiner et al. |
| 10,315,031 | B2 | 6/2019 | Brink et al. |
| 10,426,949 | B2 | 10/2019 | Johnson et al. |
| 10,561,848 | B2 | 2/2020 | Xiao et al. |
| 10,569,088 | B2 | 2/2020 | Dinsmoor et al. |
| 10,576,283 | B2 | 3/2020 | Flaherty et al. |
| 10,576,293 | B2 | 3/2020 | Peterson et al. |
| 10,625,082 | B2 | 4/2020 | Laghi |
| 10,716,505 | B2 | 7/2020 | Blum et al. |
| 10,729,903 | B2 | 8/2020 | Jiang et al. |
| 11,045,649 | B2 | 6/2021 | Wei et al. |
| 2003/0158583 | A1 | 8/2003 | Burnett et al. |
| 2004/0193228 | A1 | 9/2004 | Gerber |
| 2007/0100388 | A1 | 5/2007 | Gerber |
| 2007/0162086 | A1 | 7/2007 | DiLorenzo |
| 2008/0300449 | A1 | 12/2008 | Gerber et al. |
| 2011/0071589 | A1 | 3/2011 | Starkebaum et al. |
| 2012/0136413 | A1 | 5/2012 | Bonde et al. |
| 2012/0197338 | A1 | 8/2012 | Su et al. |
| 2013/0079840 | A1 | 3/2013 | Su et al. |
| 2013/0079841 | A1 | 3/2013 | Su et al. |
| 2014/0046397 | A1 | 2/2014 | Rohrer et al. |
| 2014/0364920 | A1 | 12/2014 | Doan et al. |
| 2016/0004547 | A1 | 1/2016 | Mitsuyu |
| 2016/0045724 | A1 | 2/2016 | Lee et al. |
| 2016/0136420 | A1 | 5/2016 | Brink et al. |
| 2017/0065821 | A1 | 3/2017 | Brink et al. |
| 2017/0239470 | A1 | 8/2017 | Wei et al. |
| 2018/0133484 | A1 | 5/2018 | Dinsmoor et al. |
| 2018/0154144 | A1 | 6/2018 | Brink et al. |
| 2018/0289965 | A1 | 10/2018 | Nelson et al. |
| 2019/0001135 | A1 | 1/2019 | Yoo et al. |
| 2019/0001139 | A1 | 1/2019 | Mishra et al. |
| 2019/0060647 | A1 | 2/2019 | Su et al. |
| 2019/0217092 | A1 | 7/2019 | Baynham et al. |
| 2019/0255331 | A1 | 8/2019 | Subbaroyan |
| 2019/0262609 | A1 | 8/2019 | Brill et al. |
| 2019/0269924 | A1 | 9/2019 | Su et al. |
| 2019/0328303 | A1 | 10/2019 | Nelson et al. |
| 2020/0046974 | A1 | 2/2020 | Ostroff et al. |
| 2020/0147397 | A1* | 5/2020 | Huertas Fernandez ..................... A61N 1/36189 |
| 2020/0230406 | A1 | 7/2020 | Brink et al. |
| 2020/0282213 | A1 | 9/2020 | Tesfayesus et al. |
| 2021/0031032 | A1 | 2/2021 | Zirpel et al. |
| 2021/0031033 | A1 | 2/2021 | Davies et al. |
| 2021/0299442 | A1 | 9/2021 | Wei et al. |

FOREIGN PATENT DOCUMENTS

| | | |
|---|---|---|
| WO | 2000/19939 A1 | 4/2000 |
| WO | 2003/026738 A1 | 4/2003 |
| WO | 2006/012423 A1 | 2/2006 |
| WO | 2007/098202 A2 | 8/2007 |
| WO | 2011/156288 A2 | 12/2011 |
| WO | 2016/028608 A1 | 2/2016 |
| WO | 2017/142948 A1 | 8/2017 |

OTHER PUBLICATIONS

Amend et al., How Does Sacral Modulation Work Best? Placement and Programming Techniques to Maximize Efficacy,: Current Urology Reports, vol. 12, No. 5, Jun. 2011, 9 pp.

Cadish et al., "Stimulation Latency and Comparison of Cycling Regimens in Women Using Sacral Neuromodulation," Neurourology and Urodynamics, vol. 36, No. 2, Feb. 2017, 4 pp.

Oerlemans et al., "Is on-Demand Sacral Neuromodulation in Patients With OAB Syndrome a Feasible Therapy Regime?", Neurourology and Urodynamics, vol. 30, No. 8, Nov. 2011, 4 pp.

Pineau et al., "Treating epilepsy via adaptive neurostimulation: a reinforcement learning approach." International Journal of Neural Systems, vol. 19, No. 4, Aug. 2009, 14 pp.

Price et al., "Prospective Randomized Crossover Trial Comparing Continuous and Cyclic Stimulation in InterStem Therapy," Female Pelvic Medicine & Reconstructive Surgery, vol. 21, No. 6, Nov./Dec. 2015, 4 pp.

Sandler et al., "Designing Patient-Specific Optimal Neurostimulation Patterns for Seizure Suppression," Neural Computation, vol. 30, No. 5, May 2018, 29 pp.

International Search Report and Written Opinion of International Application No. PCT/US2021/026415, mailed Aug. 11, 2021, 14 pp.

U.S. Appl. No. 17/453,611, filed Nov. 4, 2021, naming Offutt et al.

* cited by examiner

PATIENT SPECIFIC OPTIMIZATION ALGORITHM

This application claims the benefit of U.S. Provisional Patent Application No. 63/009,710, filed 14 Apr. 2020, the entire contents of which is incorporated herein by reference.

TECHNICAL FIELD

The disclosure relates to determining medical device settings and, more particularly, determining settings for medical devices that deliver therapy to a patient.

BACKGROUND

Disease, age, and injury may impair physiological functions of a patient. In some situations, the physiological functions are completely impaired. In other examples, the physiological function may operate sufficiently at some times or under some conditions and operate inadequately at other times or under other conditions. Some examples of impaired physiological functions include overactive bladder, non-obstructive urinary retention, fecal incontinence, constipation, pelvic pain, and sexual dysfunction. In one example, bladder dysfunction, such as overactive bladder, urgency, or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, or urinary incontinence that interferes with normal physiological function. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. In some cases, urinary incontinence may be attributed to improper sphincter function, either in the internal urinary sphincter or external urinary sphincter.

Electrical nerve stimulation may be used for several therapeutic and diagnostic purposes, including the treatment of urinary incontinence. Electrical nerve stimulation may be delivered by devices with a limited power source (e.g., implantable devices that use a battery). Power consumption may be a limiting factor in the effectiveness and viability of such devices. Additionally, a body may adapt to continuous stimulation.

SUMMARY

In general, the disclosure is directed to devices, systems, and techniques for determining, maintaining, and re-gaining effective stimulation therapy settings for a patient. The example techniques are described with respect to neurostimulation but may be extended to other types of stimulation as well. Typically, when a patient is evaluated for a potential neurostimulation implant, a patient may interface with a trial system under the supervision of a medical healthcare worker and the medical healthcare worker may test various stimulation program settings on the patient. For example, the medical healthcare worker may test different stimulation program settings, such as neurostimulation programs, neurostimulation parameters (e.g., at least one of a current or voltage amplitude of the stimulation signal, a frequency or pulse rate of the stimulation signal, the shape of the stimulation signal waveform, a duty cycle of the stimulation signal, a pulse width of the stimulation signal, duty cycling of the stimulation ON/OFF periods, etc.) and/or the combination of electrodes and respective polarities of the electrodes used to deliver the stimulation. If the patient is responsive to the neurostimulation therapy, the patient may undergo an implantation procedure. After implantation, the medical healthcare worker may again test various stimulation program settings. The testing of stimulation program settings may occur over several office visits during which the medical healthcare worker attempts to find stimulation program settings that are therapeutic to the patient. Arriving at therapeutic stimulation program settings is generally attained through a trial and error process for a particular patient. While one patient may find particular stimulation program settings to provide symptom relief, another patient may not. In some instances, stimulation program settings that may provide symptom relief to one patient may even be uncomfortable to another patient.

Patients may suffer from different diseases, different states of disease progression, and have different medical histories. Patients may be on different medications and have different lifestyles. The differences between patients may lead to a need to customize stimulation therapy to a given patient by determining stimulation program settings, such as neurostimulation programs, neurostimulation parameters and/or combination of active electrodes, that may be therapeutic for that particular patient. This disclosure provides techniques for initially and longitudinally (e.g., over time) customizing the timing and parameters of neurostimulation therapy delivery throughout the therapy and patient management lifecycle at a level of a specific patient population cohort (e.g., diagnosis) and/or an individual patient (personalized medicine). These techniques may reduce management burdens for patients and physicians. For example, the techniques of this disclosure may decrease the time it takes to find a therapeutic neurostimulation treatment for a patient thereby reducing the duration or frequency of unpleasant symptoms or decrease the number of office visits required to find a therapeutic neurostimulation treatment for the patient. Additionally, these techniques may enable more efficient use of an implanted medical device (IMD). For example, by reducing the time required to find a therapeutic neurostimulation treatment for the patient, the stimulation program settings of the IMD may be more quickly optimized than the stimulation program settings otherwise would be, which may result in more efficient power usage or a reduction in communications needed with the IMD. Moreover, some patients may lose efficacy as they habituate to therapy or due to other environmental factors, such as aging or new medications. The techniques described herein may assist such patients.

While many of the techniques of this disclosure are described herein as being implemented on a server in a cloud computing environment, it should be noted that the techniques may be implemented on an implantable medical device (IMD), on an external device or the server or any combination thereof. According to the techniques of this disclosure, a system may collect information relating to a patient and population-informed information and determine stimulation program settings based on the information relating to the patient and the population-informed information. The system may take the patient through a plurality of periods during which different stimulation program settings, such as neurostimulation programs, neurostimulation parameters and/or electrode combinations, are utilized. The system may receive information relating to the efficacy of the stimulation program settings. The system may determine initial stimulation program settings and maintenance stimulation program settings based on the information captured and the population-informed information.

In one example, the disclosure is directed to a system for determining neurostimulation therapy, the system comprising memory population-informed configured to store first information relating to a patient, wherein the first information is captured during a baseline period that is prior to the patient receiving stimulation, and processor circuitry coupled to the memory, the processor circuitry being configured to receive the first information relating to the patient, receive second information relating to the patient, wherein the second information is captured during an initial therapy assignment and the second information comprises testing data generated by delivering stimulation during an implant procedure, determine initial stimulation program settings based on the first information, the second information and population-informed information, the population-informed information being related to other patients, and cause, during a training period, delivery of therapy based on the initial stimulation program settings.

In another example, the disclosure is directed to a method comprising receiving first information relating to a patient, wherein the first information is captured during a baseline period that is prior to the patient receiving stimulation, receiving second information relating to the patient, wherein the second information is captured during an initial therapy assignment and the second information comprises testing data generated by delivering stimulation during an implant procedure, determining initial stimulation program settings based on the first information, the second information and population-informed information, the population-informed information being related to other patients, and causing, during a training period, delivery of therapy based on the initial stimulation program settings.

In a further aspect, the disclosure is directed to a non-transitory storage medium containing instructions which when executed by one or more processors, cause the one or more processors to receive first information relating to a patient, wherein the first information is captured during a baseline period that is prior to the patient receiving stimulation, receive second information relating to the patient, wherein the second information is captured during an initial therapy assignment and the second information comprises testing data generated by delivering stimulation during an implant procedure, determine initial stimulation program settings based on the first information, the second information and population-informed information, the population-informed information being related to other patients, and cause, during a training period, delivery of therapy based on the initial stimulation program settings.

In another aspect, this disclosure is directed to an implantable medical device comprising memory configured to store initial stimulation program settings, wherein the initial stimulation program setting are determined based on first information relating to a patient captured during a baseline period that is prior to the patient receiving stimulation, second information captured during an initial therapy assignment including testing data generated by delivering stimulation during an implant procedure of the IMD, and population-informed information related to other patients, and processor circuitry configured to cause a stimulation generator to deliver therapy based on the initial stimulation program setting during a training period.

The details of one or more examples are set forth in the accompanying drawings and the description below. Other features, objects, and advantages of the disclosure will be apparent from the description and drawings, and from the claims.

The above summary is not intended to describe each illustrated example or every implementation of the present disclosure.

DETAILED DESCRIPTION

Figure 1:
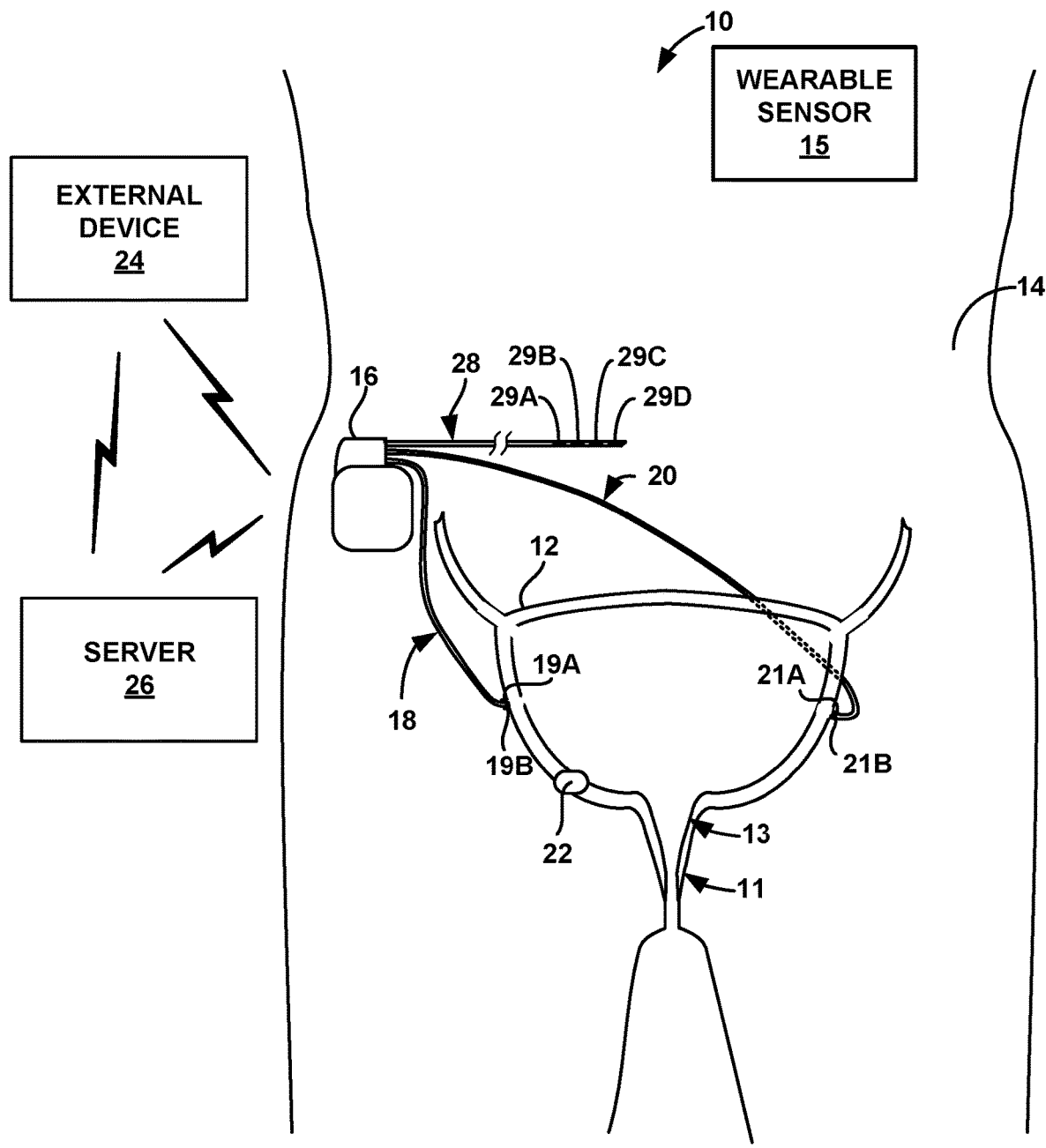
FIG. 1 is a conceptual diagram illustrating an example system that manages delivery of neurostimulation to a patient to manage bladder dysfunction, such as overactive bladder, urgency, or urinary incontinence.

The present disclosure is directed to devices, systems, and techniques for determining stimulation program settings for neurostimulation therapy for a patient. This disclosure covers techniques to integrate patient data to create and maintain customized, distributed and closed-loop algorithms for determining stimulation program settings for therapy delivery for neuromodulation, such as sacral neuromodulation. The patient data may include individual and population data. The patient data may be self-reported and/or automatically measured/recorded, for example, by sensors which may be external to the patient or internal to the patent (e.g., attached to an implantable medical device (IMD), such as a neurostimulation device). In some examples, the self-reported patient data may include demographic information and the patient's medical history. In some examples, the sensor data may include data indicative of a physiological marker, such as a bladder fill stage or a voiding event, which may be indicative of the efficacy of stimulation program settings. The techniques of this disclosure may include applying various algorithms within defined specific phases of therapy and patient management lifecycles to achieve adaptive and customized timing and stimulation setting(s) of therapy delivery.

The techniques may be used to customize therapy for a variety of dysfunctions, diseases or disorders. For purposes of illustration, but without limitation, use of the techniques will be described below with respect to bladder dysfunction. Bladder dysfunction generally refers to a condition of improper functioning of the bladder or urinary tract, and may include, for example, an overactive bladder, urgency, or urinary incontinence. Overactive bladder (OAB) is a patient condition that may include symptoms, such as urgency, with or without urinary incontinence. Urgency is a sudden, compelling urge to urinate, and may often, though not always, be associated with urinary incontinence. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence. Other bladder dysfunctions may include disorders such as non-obstructive urinary retention.

One type of therapy for treating bladder dysfunction includes delivery of electrical stimulation to a target tissue site within a patient to cause a therapeutic effect during delivery of the electrical stimulation. The delivery of electrical stimulation may be continuous, may cycle on and off, or be on during certain times and off during certain times. This therapeutic effect may be sustained even for periods of time when the electrical stimulation is off. For example, delivery of electrical stimulation from an IMD to a target therapy site, e.g., a tissue site directly or indirectly involved with modulating the activity of a spinal nerve (e.g., a sacral nerve), a pudendal nerve, dorsal genital nerve, a tibial nerve, a saphenous nerve, an inferior rectal nerve, a perineal nerve, branches of any of the aforementioned nerves, roots of any of the aforementioned nerves, ganglia of any of the aforementioned nerves, or plexus of any of the aforementioned nerves, may provide an immediate therapeutic effect for bladder dysfunction, such as a desired reduction in frequency of bladder contractions. In some cases, electrical stimulation of the sacral nerve may modulate afferent nerve activities to restore urinary function during the electrical stimulation.

For instance, a medical device, such as an IMD, may be configured to target the sacral nerve using electrical stimulation (sacral neuromodulation (SNM)). The stimulation of the sacral nerve may provide therapy for various pelvic dysfunctions, particularly disorders of pelvic floor function. Examples of pelvic dysfunctions include, but are not necessarily limited to, overactive bladder, non-obstructive urinary retention, fecal incontinence, constipation, pelvic pain, and sexual dysfunction. The medical device may deliver stimulation therapy to at least one nerve (e.g., spinal nerve or a pelvic floor nerve) to modulate activity of the nerve via at least one electrode electrically connected to the medical device. The electrical stimulation may be configured to modulate contraction of a detrusor muscle of the patient to cause a decrease in frequency of bladder contractions (to reduce incontinence) or an increase in the frequency of bladder contractions (to promote voiding). Reduction in frequency of bladder contractions may reduce urgency of voiding and may reduce urgency and/or urinary incontinence, and thereby at least partially alleviate bladder dysfunction.

The neurostimulation described herein may be targeted to manage bladder dysfunction, such as an overactive bladder, urgency, urinary incontinence, or even non-obstructive urinary retention. For example, the stimulation may be delivered to target tissue sites normally used to alleviate these types of dysfunction. Although the techniques are primarily described in this disclosure for managing bladder dysfunction, the techniques may also be applied to manage other pelvic floor disorders or disorders relating to other organs, tissues or nerves of the patient. For example, the devices, systems, and techniques described in this disclosure alternatively or additionally may be utilized to manage sexual dysfunction, pelvic pain, fecal urgency or fecal incontinence. Example nerves that may be targeted for therapy include sacral nerves, pudendal nerves, a dorsal nerve of the penis or clitoris, tibial nerves, saphenous nerves, sural nerves, sciatic nerves, the inferior rectal nerve, and peroneal or perineal nerves. Example organ systems that may be treated for dysfunction may include the large and small bowel, stomach and/or intestines, liver, and spleen, which may be modulated by delivering neurostimulation directly to the organs, to one or nerves innervating the organ, and/or blood supplies reaching the organs. In some examples, the techniques described in this disclosure may be utilized for spinal cord stimulation (e.g., for pain therapy) or for deep brain stimulation (DBS) (e.g., for neurological disorders like Parkinson's disease).

Various examples are discussed relative to one or more stimulation devices. It is recognized that the stimulation devices may include features and functionality in addition to electrical stimulation. Many of these additional features are expressly discussed herein. A few example features include, but are not limited to, different types of sensing capabilities and different types of wireless communication capabilities. For ease of discussion, the present disclosure does not expressly recite every conceivable combination of the additional features, such as by repeating every feature each time different examples and uses of the stimulation devices are discussed.

FIG. 1 is a conceptual diagram illustrating an example system 10 that determines stimulation setting(s) and manages delivery of neurostimulation to patient 14 to manage bladder dysfunction, such as overactive bladder, urgency, or urinary incontinence. As shown in the example of FIG. 1, therapy system 10 includes an implantable medical device (IMD) 16 (e.g., an example medical device), which is coupled to leads 18, 20, and 28 and sensor 22. System 10 also includes an external device 24, which is configured to communicate with IMD 16 via wireless communication. System 10 also includes server 26 which may be one or more servers in a cloud computing environment. Server 26 may be configured to communicate with external device 24 and/or IMD 16 via wireless communication through a network access point (not shown in FIG. 1) and may be collocated with external device 24 or may be located elsewhere, such as in a cloud computing data center. IMD 16 generally operates as a therapy device that delivers neurostimulation (e.g., electrical stimulation in the example of FIG. 1) to, for example, a target tissue site proximate a spinal nerve, a sacral nerve, a pudendal nerve, dorsal genital nerve, a tibial nerve, a saphenous nerve, an inferior rectal nerve, a perineal nerve, or other pelvic nerves, branches of any of the aforementioned nerves, roots of any of the aforementioned nerves, ganglia of any of the aforementioned nerves, or plexus of any of the aforementioned nerves. IMD 16 provides electrical stimulation to patient 14 by generating and delivering a programmable electrical stimulation signal (e.g., in the form of electrical pulses or an electrical waveform) to a target a therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, 21B, 29A, 29B, 29C, and 29D) and stimulation electrodes, such as electrodes 29, to sensing circuitry and a stimulation delivery circuitry (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases. In some examples, system 10 may include electrodes (such as electrodes 19 and 21), a strain gauge, one or more accelerometers, ultrasound sensors, optical sensors, or any other sensor. In some examples, the sensors may be configured to gather information relating to the patient, such as detect contractions of bladder 12, pressure or volume of bladder 12, or any other indication of the fill cycle of bladder 12 and/or possible bladder dysfunctional states. In some examples, system 10 may use sensors other than electrodes 19 and 21 for sensing information relating to the patient, such as bladder volume. System 10 may use the sensor data for determining stimulation program settings for a given patient, as discussed below. IMD 16 may communicate sensed data to server 26. In some examples, IMD 16 may communicate the sensor data through external device 24. In other examples, IMD 16 may communicate the sensor data to server 26 without communicating the sensor data through external device 24.

In some examples, system 10 may not use any sensors at all. For example, external device 24 may collect user input identifying a voiding event, perceived level of fullness, or any other indication of an event associated with the patient. The user input may be in the form of a voiding journal analyzed by external device 24, IMD 16 or server 26, or individual user inputs associated with respective voiding events, leakage, or any other event related to the patient. External device 24 may provide this user input to server 26.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal (e.g., sacral) or pudendal nerve. For example, lead 28 may be positioned such that electrodes 29 deliver electrical stimulation to a spinal, sacral or pudendal nerve to reduce a frequency and/or magnitude of contractions of bladder 12. Additional electrodes of lead 28 and/or electrodes of another lead may provide additional stimulation therapy to other nerves or tissues as well. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects (e.g., therapeutic effects). In examples, one or more of leads 18, 20, 28 may be, at least in part, paddle-shaped (e.g., a "paddle" lead), and may include an array of electrodes on a common surface, which may or may not be substantially flat.

In some examples, one or more of electrodes 19, 20, 29 may be cuff electrodes that are configured to extend at least partially around a nerve (e.g., extend axially around an outer surface of a nerve). Delivering electrical stimulation via one or more cuff electrodes and/or segmented electrodes may help achieve a more uniform electrical field or activation field distribution relative to the nerve, which may help minimize discomfort to patient 14 that results from the delivery of electrical stimulation. An electrical field may define the volume of tissue that is affected when the electrodes 19, 20, 29 are activated. An activation field represents the neurons that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies or other electrical stimulations to respective stimulation sites within patient 14 or for monitoring at least one physiological marker of patient 14.

In accordance with some examples of the disclosure, IMD 16 delivers electrical stimulation to at least one of a spinal nerve (e.g., a sacral nerve), a pudendal nerve, dorsal genital nerve, a tibial nerve, a saphenous nerve, an inferior rectal nerve, or a perineal nerve to provide a therapeutic effect that reduces or eliminates a dysfunctional state such as overactive bladder. The desired therapeutic effect may be an inhibitory physiological response related to voiding of patient 14, such as a reduction in bladder contraction frequency by a desired level or degree (e.g., percentage).

A stimulation program may define various parameters of the stimulation waveform and electrode configuration which result in a predetermined stimulation intensity being delivered to the targeted nerve or tissue. In some examples, the stimulation program defines parameters for at least one of a current or voltage amplitude of the stimulation signal, a frequency or pulse rate of the stimulation, the shape of the stimulation waveform, a duty cycle of the stimulation, a pulse width of the stimulation, a duty cycle of the stimulation ON/OFF periods, and/or the combination of electrodes 29 and respective polarities of the subset of electrodes 29 used to deliver the stimulation. Together, these stimulation parameter values may be used to define the stimulation intensity (also referred to herein as a stimulation intensity level). In some examples, if stimulation pulses are delivered in bursts, a burst duty cycle also may contribute to stimulation intensity. Also, independent of intensity, a particular pulse width and/or pulse rate may be selected from a range suitable for causing the desired therapeutic effect after stimulation is terminated and, optionally, during stimulation. In addition, as described herein, a period during which stimulation is delivered may include on and off periods (e.g., a duty cycle or bursts of pulses) where even the short inter-pulse durations of time when pulses are not delivered are still considered part of the delivery of stimulation. A period during which system 10 withholds stimulation delivery is a period in which no stimulation program is active for IMD 16 (e.g., IMD 16 is not tracking pulse durations or inter-pulse durations that occur as part of the electrical stimulation delivery scheme). In addition to the above stimulation parameters, the stimulation may be defined by other characteristics, such as a time for which stimulation is delivered, a time for which stimulation is terminated, and times during which stimulation is withheld.

System 10 may also include an external device 24, as shown in FIG. 1. External device 24 may be an example of a computing device (such as computing devices 230A-230N shown in FIG. 4). In some examples, external device 24 may be a clinician programmer or patient programmer. In some examples, external device 24 may be a device for inputting information relating to a patient. In some examples, external device 24 may be a wearable communication device, with a therapy request input integrated into a key fob or a wristwatch, handheld computing device, smart phone, computer workstation, or networked computing device. External device 24 may include a user interface that is configured to receive input from a user (e.g., patient 14, a patient caretaker or a clinician). In some examples, the user interface includes, for example, a keypad and a display, which may for example, be a liquid crystal display (LCD) or light emitting diode (LED) display. In some examples, the user interface may include a turnable knob or a representation of a turnable knob. The keypad may take the form of an alphanumeric keypad or a reduced set of keys associated with particular functions. External device 24 may additionally or alternatively include a peripheral pointing device, such as a mouse, via which a user may interact with the user interface. In some examples, a display of external device 24 may include a touch screen display, and a user may interact with external device 24 via the display. It should be noted that the user may also interact with external device 24, server 26 and/or IMD 16 remotely via a networked computing device.

A user, such as a physician, technician, surgeon, electrophysiologist, or other clinician, may also interact with external device 24 or another separate programmer (not shown), such as a clinician programmer, to communicate with IMD 16 and/or server 26. Such a user may interact with external device 24 to retrieve physiological or diagnostic information from IMD 16. The user may also interact with external device 24 to program IMD 16, e.g., select values for the stimulation parameter values with which IMD 16 generates and delivers stimulation and/or the other operational parameters of IMD 16, such as magnitudes of stimulation energy, user requested periods for stimulation or periods to prevent stimulation, or any other such user customization of therapy. In some examples, the stimulation parameter values may be proposed by system 10, for example, by server 26 and a user may be able to accept or reject the stimulation parameter values. In other examples, the stimulation parameter values may be set by system 10, for example, by server 26. As discussed herein, the user may also provide input to external device 24 indicative of physiological events such as bladder fill level perception and void events.

In some examples, a user, such as a clinician or patient, may input information relating to a patient into external device 24 and external device 24 may collect first information relating to the patient and provide that information to server 26. The first information relating to a patient may include: 1) demographic information, such as gender, age, etc.; 2) medical history, such as BMI, diagnosis, comorbidities, medications, etc.; 3) baseline symptom data during a predetermined time period, such as somewhere in the range of three days to two weeks, for example. Baseline symptom data may include symptoms of a disease that the patient is experiencing. For example, baseline symptom data may include a number of or time when a patient experiences an incontinence issue or a feeling of urgency to urinate. Baseline symptom data may also include volume of a urinary event or other measures indicative of the symptoms the patient may be experiencing, for example, information relating to bowel movements, pain, etc. In some examples, the patient may be prompted by external device 24 to answer questions related to their medications, lifestyle and quality of life. These questions may include questions relating to length and quality of sleep, fluid intake, food intake, food choices, activities of daily life, level of activities (e.g., step counts), exercise, pain, discomfort, etc. In some examples, these questions may be asked periodically over a period of days, such as three to four days. In some examples, the user may provide the first information relating to a patient prior to beginning treatment, during a baseline period. In other examples, the first information related to the patient's medications, lifestyle and quality of life may be gathered in another manner, such as entered by a clinician onto external device 24. In some example, the user may provide further information relating to a patient during other periods. For example, external device 24 may prompt patient 14 to answer questions about their symptoms or the efficacy of treatment during the other periods. For example, external device 24 may prompt patient 14 to input whether patient 14 had a bladder leak that day or a number of times patient 14 had bladder leaks that day. External device 24 may collect the information relating to a patent and provide the information relating to the patient, including the answers to the questions, to server 26.

In some examples, a healthcare provider may utilize sensors, such as wearable sensor 15 or existing implanted sensors, to collect more objective patient data related to sleep, activity or disease symptoms. For example, wearable sensor 15 may be a heartrate sensor, an accelerometer and/or other sensor to collect patient data, for example, on disease symptoms or lifestyle. The patient data captured by the sensors, such as wearable sensor 15, may be provided to server 26. In some examples, the sensors, such as wearable sensor 15, may be configured to communicate with an external device, such as external device 24, via a wireless link. In some examples, external device 24 may collect the patient data generated by the sensors and send the patient data to server 26. In other examples, another device may collect the patient data generated by the sensors and send the patient data to server 26.

For example, the user may use external device 24 to retrieve information from IMD 16 relating to the contraction frequency of bladder 12 and/or voiding events. As another example, the user may use external device 24 to retrieve information from IMD 16 relating to the performance or integrity of IMD 16 or other components of system 10, such as leads 18, 20, and 28, or a power source of IMD 16. In some examples, this information may be presented to the user as an alert if a system condition that may affect the efficacy of therapy is detected.

The user of external device 24 may also communicate with server 26. For example, the user of external device 24 may provide information relating to the patient to server 26, such as demographic information, medical history, lifestyle information, bladder events, level satisfaction with therapy or sensor data.

Patient 14 may, for example, use a keypad or touch screen of external device 24 to request IMD 16 to deliver or terminate the electrical stimulation, such as when patient 14 senses that a leaking episode may be imminent or when an upcoming void may benefit from terminating therapy that promotes urine retention. In this way, patient 14 may use external device 24 to provide a therapy request to control the delivery of the electrical stimulation "on demand," e.g., when patient 14 deems the second stimulation therapy desirable. This request may be a therapy trigger event used to terminate electrical stimulation. Patient 14 may also use external device 24 to provide other information to IMD 16, such as information indicative of a phase of a physiological cycle, such as the occurrence of a voiding event.

External device 24 may provide a notification to patient 14 when the electrical stimulation is being delivered or notify patient 14 of the prospective termination of the electrical stimulation. In addition, notification of termination may be helpful so that patient 14 knows that a voiding event may be more probable and/or the end of the fill cycle is nearing such that the bladder should be emptied (e.g., the patient should visit a restroom). In such examples, external device 24 may display a visible message, emit an audible alert signal or provide a somatosensory alert (e.g., by causing a housing of external device 24 to vibrate). In other examples, the notification may indicate when therapy is available (e.g., a countdown in minutes, or indication that therapy is ready) during the physiological cycle. In this manner, external device 24 may wait for input from patient 14 prior to terminating the electrical stimulation that reduces bladder contraction or otherwise promotes urine retention. Patient 14 may enter input that either confirms termination of the electrical stimulation so that the therapy stops for voiding purposes, confirms that the system should maintain therapy delivery until patient 14 may void, and/or confirms that patient 14 is ready for another different stimulation therapy that promotes voiding during the voiding event.

In the event that no input is received within a particular range of time when a voiding event is predicted, external device 24 may wirelessly transmit a signal that indicates the absence of patient input to IMD 16. IMD 16 may then elect to continue stimulation until the patient input is received, or terminate stimulation, based on the programming of IMD 16. In some examples, the termination or continuation of electrical stimulation may be responsive to other physiological markers.

IMD 16 and external device 24 may communicate via wireless communication using any techniques known in the art. Examples of communication techniques may include, for example, low frequency or radiofrequency (RF) telemetry, but other techniques are also contemplated. In some examples, external device 24 may include a programming lead that may be placed proximate to the patient's body near the IMD 16 implant site in order to improve the quality or security of communication between IMD 16 and external device 24.

In the example four-wire arrangement shown in FIG. 1, electrodes 19A and 21A and electrodes 19B and 21B, may be located substantially opposite each other relative to the center of bladder 12. For example, electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMB 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMB 16 determines the impedance of bladder 12 using a known value of the electrical signal sourced the determined voltage.

In other examples, electrodes 19 and 21 may be used to detect an electromyogram (EMG) of the detrusor muscle. This EMG may be used to determine the frequency of bladder contractions and the physiological marker of patient 14. The EMG may also be used to detect the strength of the bladder contractions in some examples. As an alternative, or in addition, to an EMG, a strain gauge or other device may be used to detect the status of bladder 12, e.g., by sensing forces indicative of bladder contractions.

In the example of FIG. 1, IMD 16 also may include a sensor 22 for detecting changes in the contraction of bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which system 10 provides therapy to manage fecal urgency or fecal incontinence), or any combination thereof. In examples in which sensor 22 is a pressure sensor, the pressure sensor may be a remote sensor that wirelessly transmits signals to IMB 16 or may be carried on one of leads 18, 20, or 28 or an additional lead coupled to IMD 16. In some examples, IMD 16 may determine whether a contraction frequency of bladder 12 has occurred based on a pressure signal generated by sensor 22.

In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples, IMD 16 may control the timing of the delivery of the electrical stimulation based on input received from sensor 22.

Sensor 22 may comprise a patient motion sensor that generates a signal indicative of patient activity level or posture state. In some examples, IMD 16 may terminate the delivery of the electrical stimulation to patient 14 upon detecting a patient activity level exceeding a particular threshold based on the signal from the motion sensor. In other examples, IMD 16 may use sensor 22 to identify posture states known to require the desired therapeutic effect. For example, patient 14 may be more prone to an involuntary voiding event when patient 14 is in an upright posture state compared to a lying down posture state. In any event, electrodes 19 and 21 and sensor 22 may be configured to detect voiding events and/or the magnitude of a fill level of bladder 12 during the fill cycle.

As discussed above, system 10 may monitor the fill cycle of bladder 12 by detecting subsequent voiding events over time. In some examples, system 10 may detect voiding events by receiving an indication of a user input (e.g., via external device 24) representative of an occurrence of a voiding event. In other words, external device 24 may receive input from the user identifying that a voiding event occurred, the beginning of a voiding event, and/or the end of the voiding event. In other examples, system 10 may automatically detect voiding events without receiving user input via external device 24. System 10 may instead detect voiding events by detecting at least one of a pressure of the bladder, a flow of urine from the bladder, a wetness of an article external of the patient, a volume of the bladder, an EMG signal, a nerve recording, a posture change, a physical location of the patient within a structure such as a house or care facility, or a toilet use event. Some sensors external to patient 14 may communicate with external device 24 and/or IMD 16 to provide this information indicative of likely voiding events. For example, wetness may be detected by a moisture sensor (e.g., electrical impedance or chemical sensor) embedded in an undergarment worn by the patient and transmitted to IMD 16 or external device 24. Similarly, a toilet may include a presence sensor that detects when a patient is using the toilet (e.g., an infrared sensor, thermal sensor, or pressure senor) and transmits a signal indicating the presence of the patient to IMD 16 or external device 24. In this manner, non-invasively obtained data may provide information indicative of voiding events without implanted sensors. The information indicative of voiding events may be provided to server 26 by external device 24 or IMD 16. System 10 of FIG. 1 may implement the techniques of this disclosure.

For example, system 10 may include memory configured to store first information relating to a patient, wherein the first information is captured during a baseline period that is prior to the patient receiving stimulation, and processor circuitry coupled to the memory, the processor circuitry being configured to receive the first information relating to the patient, receive second information relating to the patient, wherein the second information is captured during an initial therapy assignment and the second information comprises testing data generated by delivering stimulation during an implant procedure, determine initial stimulation program settings based on the first information, the second information and population-informed information, the population-informed information being related to other patients, and cause, during a training period, delivery of therapy based on the initial stimulation program settings.

Figure 2A:
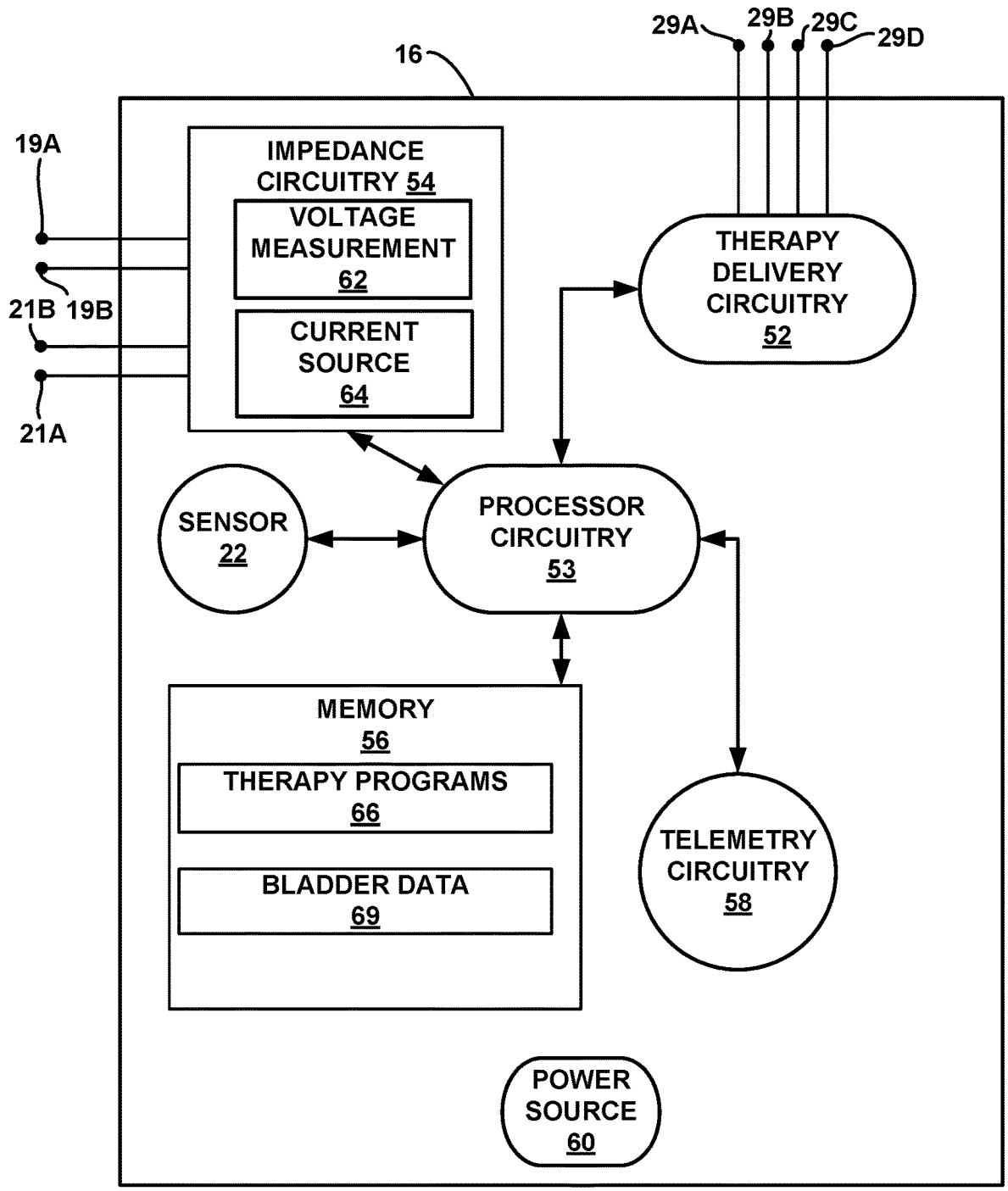
FIGS. 2A and 2B are block diagrams illustrating example configurations of implantable medical devices (IMDs) which may be utilized in the system of FIG. 1.

FIG. 2A is a block diagram illustrating an example configuration of an IMD which may be utilized in the system of FIG. 1. As shown in FIG. 2A, IMD 16 includes sensor 22, processor circuitry 53, therapy delivery circuitry 52, impedance circuitry 54, memory 56, telemetry circuitry 58, and power source 60. In other examples, IMD 16 may include a greater or fewer number of components. For example, in some examples, such as examples in which IMD 16 deliver the electrical stimulation in an open-loop manner, IMD 16 may not include sensor 22 (e.g., a pressure sensor or electrical signal sensors) and/or impedance circuitry 54. In some examples, physiological markers may be provided via patient input on an external device if no sensors (e.g., sensor 22 and/or impedance circuitry 54) are included with IMD 16.

According to some examples, processor circuitry 53 identifies changes to the patient's physiological state that are relevant to desired changes in neurostimulation. For example, voiding of the bladder may indicate that stimulation is not required for a certain time or until sensor input indicates otherwise. The system may include one or more sensors that sense biomarkers indicative of a change in the relevant physiological state(s), e.g., sensor 22 and/or sensors external to IMD 16. For example, a pressure sensor may detect the amount of bladder pressure. Thus, processor circuitry 53 may be configured to classify certain changes in bladder pressure as corresponding to a void (e.g., when the sensed signals match one or more sets of parameters). Processor circuitry 53 may also classify the relative fullness of the bladder from subsequently detected pressure levels.

Specified parameters of the bladder pressure signal may be used to inform processor circuitry 53 to identify when voiding events have occurred. For instance, and without limitation, processor circuitry 53 may monitor one or more of bladder pressure, the amount of change in bladder pressure, the duration of change in bladder pressure, and the rate of change in bladder pressure. This data may serve to identify a voiding event. It should be noted that other nerve targets may alter urinary function in a manner that is similar to sacral nerves, such as the tibial nerve, saphenous nerve, pudendal nerve, dorsal nerve of the penis, and the dorsal nerve of the clitoris.

In general, IMD 16 may comprise any suitable arrangement of hardware, alone or in combination with software and/or firmware, to perform the techniques attributed to IMD 16 and processor circuitry 53, therapy delivery circuitry 52, impedance circuitry 54, and telemetry circuitry 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, may include, in various examples, a memory 56, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor circuitry 53, therapy delivery circuitry 52, impedance circuitry 54, and telemetry circuitry 58 are described as separate circuitry, in some examples, processor circuitry 53, therapy delivery circuitry 52, impedance circuitry 54, and telemetry circuitry 58 are functionally integrated. In some examples, processor circuitry 53, therapy delivery circuitry 52, impedance circuitry 54, and telemetry circuitry 58 correspond to individual hardware units, such as microprocessors, ASICs, DSPs, FPGAs, or other hardware units. In further examples, any of processor circuitry 53, therapy delivery circuitry 52, impedance circuitry 54, and telemetry circuitry 58 may correspond to multiple individual hardware units such as microprocessors, ASICs, DSPs, FPGAs, or other hardware units.

Memory 56 stores therapy programs 66 that specify stimulation parameter values for the electrical stimulation provided by IMD 16. Therapy programs 66 may also store information relating to determining and using physiological markers, information relating to physiological cycles and/or dysfunctional states, or any other information. In some examples, IMD 16 may deliver stimulation therapy based on one or more physiological markers. In other examples, IMD 16 may deliver stimulation therapy that is not based on one or more physiological markers. In some examples, memory 56 also stores bladder data 69, which processor circuitry 53 may use for controlling the timing of the delivery of the electrical stimulation (e.g., phases of physiological cycles that define when to deliver and withhold stimulation). For example, bladder data 69 may include threshold values or baseline values for at least one of bladder impedance, bladder pressure, sacral or pudendal afferent nerve signals, bladder contraction frequency, or external urinary sphincter EMG templates for use as physiological markers for an associated physiological cycle. Bladder data 69 may also include timing information and physiological markers associated with physiological events, such as a voiding event.

IMD 16 may provide some or all of bladder data 69 to external device 24 or server 26.

Information related to sensed bladder contractions, bladder impedance and/or posture of patient 14 may be recorded for long-term storage and retrieval by a user, to be used by processor circuitry 53 for adjustment of stimulation parameters (e.g., amplitude, pulse width, pulse rate, duty cycle, etc.) or for use as a physiological marker, or to be sent to server 24. In some examples, memory 56 includes separate memories for storing instructions, electrical signal information, stimulation programs 66 and bladder data 69.

Generally, therapy delivery circuitry 52 generates and delivers electrical stimulation under the control of processor circuitry 53. In some examples, processor circuitry 53 controls therapy delivery circuitry 52 by accessing memory 56 to selectively access and load at least one of stimulation programs 66 to therapy delivery circuitry 52. For example, in operation, processor circuitry 53 may access memory 56 to load one of stimulation programs 66 to therapy delivery circuitry 52. In other examples, therapy delivery circuitry 52 may access memory 56 and load one of the stimulation programs 66.

By way of example, processor circuitry 53 may access memory 56 to load one of stimulation programs 66 to therapy delivery circuitry 52 for delivering the electrical stimulation to patient 14. A clinician or patient 14 may select a particular one of stimulation programs 66 from a list using a programming device, such as external device 24 or a clinician programmer. Processor circuitry 53 may receive the selection via telemetry circuitry 58. Therapy delivery circuitry 52 delivers the electrical stimulation to patient 14 according to the selected program for an extended period of time, such as minutes, hours, days, weeks, or until patient 14 or a clinician manually stops or changes the program.

Therapy delivery circuitry 52 delivers electrical stimulation according to stimulation parameters. In some examples, therapy delivery circuitry 52 delivers electrical stimulation in the form of electrical pulses. In such examples, relevant stimulation parameters may include a voltage amplitude, a current amplitude, a pulse rate, a pulse width, a duty cycle, a duty cycle of the stimulation ON/OFF periods, or the combination of electrodes 29 that therapy delivery circuitry 52 uses to deliver the stimulation signal. In other examples, therapy delivery circuitry 52 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 29 therapy delivery circuitry 52 uses to deliver the stimulation signal.

In some examples, the stimulation parameters for the stimulation programs 66 may be selected to relax bladder 12, e.g., to reduce a frequency of contractions of bladder 12, after termination of the electrical stimulation. An example range of stimulation parameters for the electrical stimulation that are likely to be effective in treating bladder dysfunction, e.g., upon application to the spinal, sacral, pudendal, tibial, saphenous, dorsal genital, inferior rectal, or perineal nerves, are as follows:

1. Frequency or pulse rate: between about 0.5 Hz and about 500 Hz, such as between about 1 Hz and about 250 Hz, between about 1 Hz and about 20 Hz, or about 10 Hz.
2. Amplitude: between about 0.1 volts and about 50 volts, such as between about 0.5 volts and about 20 volts, or between about 1 volt and about 10 volts. Alternatively, the amplitude may be between about 0.1 milliamps (mA) and about 50 mA, such as between about 0.5 mA and about 20 mA, or between about 1 mA and about 10 mA.
3. Pulse Width: between about 10 microseconds (μs) and about 5000 μs, such as between about 100 μs and about 1000 μs, or between about 100 μs and about 200 μs.

When IMD 16 is monitoring the fill level of the bladder to determine the status of the bladder fill cycle, processor circuitry 53 may monitor impedance of bladder 12 for a predetermined duration of time to detect contractions of bladder 12, and determine the baseline contraction frequency of bladder 12 by determining a number of contractions of bladder 12 in the predetermined duration of time. In other examples, electrodes 19 or 21 may be used to detect an EMG of the detrusor muscle to identify bladder contraction frequencies. Alternatively, a strain gauge sensor signal output or other measure of bladder contraction change may be used to detect the physiological marker of bladder 12. Each of these alternative methods of monitoring the fill level and/or voiding event of bladder 12 may be used in some examples.

In the example illustrated in FIG. 2A, impedance circuitry 54 includes voltage measurement circuitry 62 and current source 64, and may include an oscillator (not shown) or the like for producing an alternating signal. In some examples, as described above with respect to FIG. 1, impedance circuitry 54 may use a four-wire, or Kelvin, arrangement. As an example, processor circuitry 53 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance circuitry 54 may also include a switching circuitry (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor circuitry 53 determines an impedance value from the measure voltage values received from voltage measurement circuitry 52.

In other examples, processor circuitry 53 may monitor signals received from sensor 22 to detect contraction of bladder 12 and determine the baseline contraction frequency. In some examples, sensor 22 may be a pressure sensor for detecting changes in pressure of bladder 12, which processor circuitry 53 may correlate to contractions of bladder 12. Processor circuitry 53 may determine a pressure value based on signals received from sensor 22 and compare the determined pressure value to a threshold value stored in bladder data 69 to determine whether the signal is indicative of a contraction of bladder 12. In some implementations, processor circuitry 53 monitors pressure of bladder 12 to detect contractions of bladder 12 for a predetermined duration of time and determines a contraction frequency of bladder 12 by calculating a number of contractions of bladder 12 in the predetermined time period.

In some examples, processor circuitry 53 may cause contraction frequency information to be stored as bladder data 69 in memory 56 and may utilize the changes to contraction frequency to track the fill level of the bladder fill cycle or otherwise track the phase of the fill cycle. In some implementations, processor circuitry 53 may, automatically or under control of a user, determine the contraction frequency over the fill cycle. Processor circuitry 53 may determine that an increase in contraction frequency indicates a later phase of the fill cycle. In some examples, processor circuitry 53 may track bladder contractions using EMG signals of patient 14. In some implementations, sensor 22 may include an EMG sensor, and processor circuitry 53 may generate an EMG from the received signals generated by sensor 22. Sensor 22 may be implanted proximate to a muscle which is active when bladder 12 is contracting, such as a detrusor muscle. Processor circuitry 53 may compare an EMG captured during the second time period to EMG templates stored as bladder data 69 (e.g., a short-term running average) to determine whether the contractions of bladder 12 are indicative of particular phases of the bladder fill cycle.

In other examples, sensor 22 may be a pressure sensor and processor circuitry 53 may monitor signals received from sensor 22 during at least a portion of the second time period to detect contraction of bladder 12. In some examples, processor circuitry 53 substantially continuously monitors pressure of bladder 12, at least during the second time periods, to detect contraction of bladder 12, and determines a contraction frequency of bladder 12 by determining a number of contractions of bladder 12 in a specified time period. Sensor 22 may also provide longer-term changes in pressure to track the bladder fill status (e.g., increased bladder volume may correspond to increased bladder pressure).

In the example of FIG. 2A, therapy delivery circuitry 52 drives electrodes on a single lead 28. Specifically, therapy delivery circuitry 52 delivers electrical stimulation to tissue of patient 14 via selected electrodes 29A-29D carried by lead 28. A proximal end of lead 28 extends from the housing of IMD 16 and a distal end of lead 28 extends to a target therapy site, such as a spinal nerve (e.g., an S3 nerve), or a therapy site within the pelvic floor, such as tissue sites proximate a sacral nerve, a pudendal nerve, a tibial nerve, a saphenous nerve, a dorsal genital nerve, an inferior rectal nerve, a perineal nerve, a hypogastric nerve, a urinary sphincter, or any combination thereof. In other examples, therapy delivery circuitry 52 may deliver electrical stimulation with electrodes on more than one lead and each of the leads may carry one or more electrodes. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

As previously described, sensor 22 may comprise a pressure sensor configured to detect changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy), or any combination thereof. Additionally, or alternatively, sensor 22 may comprise a motion sensor, such as a two-axis accelerometer, three-axis accelerometer, one or more gyroscopes, pressure transducers, piezoelectric crystals, or other sensors that generate a signal that changes as patient activity level or posture state changes. Processor circuitry 53 may detect a physiological marker indicative of point during a bladder fill cycle. Sensor 22 may also be a motion sensor that is responsive to tapping (e.g., by patient 14) on skin superior to IMD 16. Processor circuitry 53 may be configured to log patient input using this tapping method (e.g., tapping may indicate that a voiding event is occurring). Alternatively, or in addition, processor circuitry 53 may control therapy circuitry 52 to deliver or terminate electrical stimulation delivery in response to the tapping or certain pattern of tapping.

In examples in which sensor 22 includes a motion sensor, processor circuitry 53 may determine a patient activity level or posture state based on a signal generated by sensor 22. This patient activity level may be, for example, sleeping, sitting, exercising, working, running, walking, or any other activity of patient 14. For example, processor circuitry 53 may determine a patient activity level by sampling the signal from sensor 22 and determining a number of activity counts during a sample period, where each activity level of a plurality of activity levels is associated with respective activity counts. In one example, processor circuitry 53 compares the signal generated by sensor 22 to one or more amplitude thresholds stored within memory 56, and identifies each threshold crossing as an activity count. The physical activity may be indicative of a fill level, a voiding event, or any other physiological marker related to the bladder fill cycle.

In some examples, processor circuitry 53 may control therapy delivery circuitry 52 to deliver or terminate the electrical stimulation based on patient input received via telemetry circuitry 58. Telemetry circuitry 58 includes any suitable hardware, firmware, software or any combination thereof for communicating with another device, such as external device 24 (FIG. 1). Under the control of processor circuitry 53, telemetry circuitry 58 may receive downlink telemetry, e.g., patient input, from and send uplink telemetry, e.g., an alert, to external device 24 with the aid of an antenna, which may be internal and/or external. Processor circuitry 53 may provide the data to be uplinked to external device 24 and the control signals for the telemetry circuit within telemetry circuitry 58, and receive data from telemetry circuitry 58.

Generally, processor circuitry 53 may control telemetry circuitry 58 to exchange information with external device 24 or another device external to IMD 16, such as server 26. Processor circuitry 53 may transmit operational information and bladder data 69 and receive stimulation programs or stimulation parameter adjustments via telemetry circuitry 58. Also, in some examples, IMD 16 may communicate with other implanted devices, such as stimulators, control devices, or sensors, via telemetry circuitry 58.

Figure 2B:
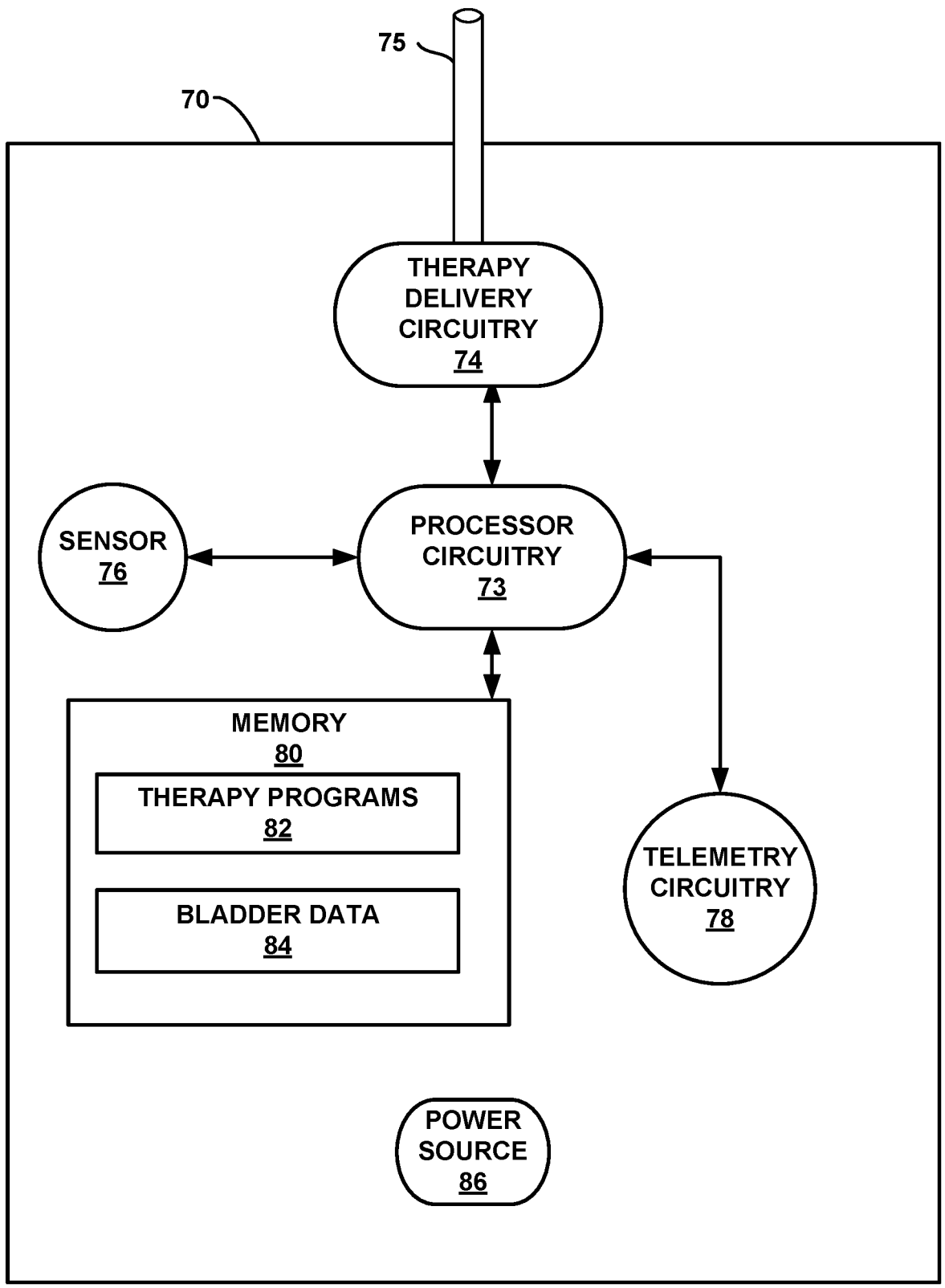

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur. IMD 16 may be configured to implement the techniques of this disclosure. For example, IMD 16 may include memory, e.g., memory 56, configured to store initial stimulation program settings, e.g., therapy programs 66, wherein the initial stimulation program setting are determined based on first information relating to a patient captured during a baseline period that is prior to the patient receiving stimulation, second information captured during an initial therapy assignment including testing data generated by delivering stimulation during an implant procedure of the IMD, and population-informed information related to other patients, and processor circuitry, e.g., processor circuitry 53, configured to cause a stimulation generator to deliver therapy based on the initial stimulation program setting during a training period. As shown in FIG. 2B, IMD 70 is similar to IMD 16 of FIG. 2A, but IMD 70 delivers neurostimulation to patient 14 in the form of drugs instead of electrical stimulation. IMD 70 includes processor circuitry 73 (e.g., similar to processor circuitry 53), therapy delivery module 74 coupled to catheter 75, sensor 76 (e.g., a pressure sensor similar to sensor 22 of FIG. 2A), telemetry circuitry 78 (e.g., similar to telemetry circuitry 58), memory 80 (e.g., similar to memory 56), and power source 86 (e.g., similar to power source 60. Although IMD 70 does not include impedance circuitry 54, this or other circuitry may be provided in some examples.

Therapy delivery module 74 may include a drug reservoir and drug pump that moves the drug from the reservoir, through catheter 75, and out to patient 14. In some examples, IMD 70 may include both a drug pump and electrical stimulation generator. Memory 80 may include therapy programs 82 and bladder data 84. Therapy programs 82 may include instructions for drug delivery. In some example, the instructions for drug delivery may be based on one or more physiological markers stored as bladder data 84. IMD 70 may deliver a bolus of drug to patient 14 based on the therapy programs. In some examples, processor circuitry 73 may predict when to deliver a bolus of drug to patient 14 based on a phase of a physiological cycle such as the bladder fill cycle, for example, in a manner similar to that of processor circuitry 53 of FIG. 2A with respect to the delivery of stimulation.

Figure 3:
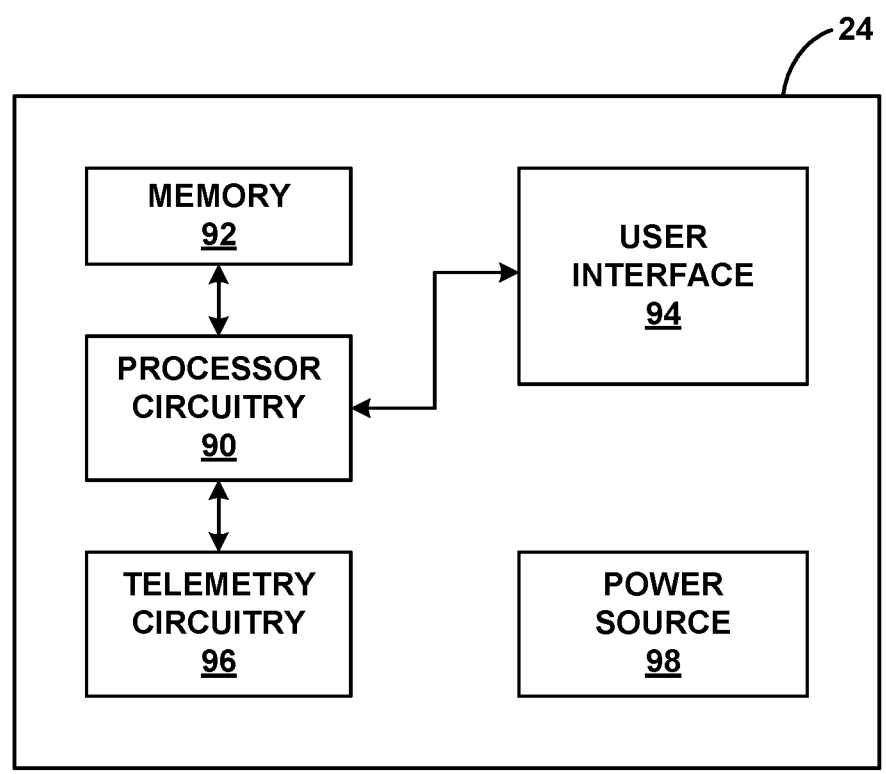
FIG. 3 is a block diagram illustrating an example configuration of an external device which may be utilized in the system of FIG. 1.

FIG. 3 is a block diagram illustrating an example configuration of an external device 24. While external device 24 may generally be described as a hand-held computing device, external device 24 may be a notebook computer, a smart phone, a workstation, a key fob, or a wearable device, for example. As illustrated in FIG. 3, external device 24 may include a processor circuitry 90, memory 92, user interface 94, telemetry circuitry 96, and power source 98. Memory 92 may store program instructions that, when executed by processor circuitry 90, cause processor circuitry 90 and external device 24 to provide the functionality ascribed to external device 24 throughout this disclosure.

In general, external device 24 comprises any suitable arrangement of hardware, alone or in combination with software and/or firmware, to perform the techniques attributed to external device 24, and processor circuitry 90, user interface 94, and telemetry circuitry 96 of external device 24. In various examples, external device 24 may include one or more processors, such as one or more microprocessors, DSPs, ASICs, FPGAs, or any other equivalent integrated or discrete logic circuitry, as well as any combinations of such components. External device 24 also, in various examples, may include a memory 92, such as RAM, ROM, PROM, EPROM, EEPROM, flash memory, a hard disk, a CD-ROM, comprising executable instructions for causing the one or more processors to perform the actions attributed to them. Moreover, although processor circuitry 90 and telemetry circuitry 96 are described as separate circuitry, in some examples, processor circuitry 90 and telemetry circuitry 96 are functionally integrated. In some examples, processor circuitry 90 and telemetry circuitry 96 and telemetry circuitry 58 correspond to individual hardware units, such as microprocessors, ASICs, DSPs, FPGAs, or other hardware units. In other examples, any of processor circuitry 90 and telemetry circuitry 96 and telemetry circuitry 58 may correspond to multiple individual hardware units, such as microprocessors, ASICs, DSPs, FPGAs, or other hardware units.

Memory 92 may store program instructions that, when executed by processor circuitry 90, cause processor circuitry 90 and external device 24 to provide the functionality ascribed to external device 24 throughout this disclosure. In some examples, memory 92 may further include program information, e.g., stimulation programs defining the neurostimulation, similar to those stored in memory 56 of IMD 16. The stimulation programs stored in memory 92 may be downloaded into memory 56 of IMD 16.

In certain examples, external device 24 includes a user interface 94 that allows the patient to provide input. A clinician or patient 14 may provide information relating to patient 14 to external device 24 through user interface 94. For example, during a baseline period, patient 14 or a clinician may input demographic information, medical history, and baseline symptom data, as discussed above. During other periods, for example, patient 14 may provide information about the symptoms or the efficacy of treatment. For example, external device 24 may prompt patient 14 through user interface 94 to input whether patient 14 had a bladder leak that day or a number of times patient 14 had bladder leaks that day.

Patient 14 may, additionally or alternatively, request a change in stimulation program or settings through user interface 94. IMD 16 may respond to patient-supplied data from the user interface providing the patient-supplied data to server 26 or by altering therapy. In some examples, patient 14 may use external device 24 (e.g., a handheld device) to record (by pushing a button) a physiological event of interest. Processor circuitry 53 of IMD 16 may respond by turning the therapy on or off, or by adjusting the therapy (e.g., the stimulation strength) or by changing the therapy program. Processor circuitry 53 may store the physiological event of interest in memory 92 for later transmission through telemetry circuitry 96 to server 26. With reference to the urological applications discussed herein, patient 14 could push a button on external device 24 (e.g., their smartphone) when the bladder is voided. This button press may cause telemetry circuitry 96 of external device 24 to send a signal to IMD 16 to turn off for a period of time. Alternatively, the patient 14 could push a button when they feel urgency of a voiding event that is about to occur. This would alert IMD 16 to turn ON, increase its therapy level or activate a specific program consistent with a pre-voiding timing scenario. Consistent with various examples of this disclosure, the patient-supplied data regarding physiological events of interest may be used as information relating to a patient by server 26 to determine stimulation program settings for patient 14.

User interface 94 may include a button or keypad, lights, a speaker for voice commands, a turnable knob, a display, such as a liquid crystal (LCD), light-emitting diode (LED), or cathode ray tube (CRT). In some examples the display may be a touch screen. As discussed in this disclosure, processor circuitry 90 may present and receive information relating to electrical stimulation and resulting therapeutic effects via user interface 94. For example, processor circuitry 90 may receive patient input via user interface 94. The input may be, for example, in the form of pressing a button on a keypad or selecting an icon from a touch screen.

Processor circuitry 90 may also present information to the patient in the form of alerts related to delivery of the electrical stimulation to patient 14 or a caregiver via user interface 94. Although not shown, external device 24 may additionally or alternatively include a data or network interface to another computing device, to facilitate communication with the other device, and presentation of information relating to the electrical stimulation and therapeutic effects after termination of the electrical stimulation via the other device.

Telemetry circuitry 96 supports wireless communication between IMD 16 and external device 24 and between server 26 and external device 24 under the control of processor circuitry 90. Telemetry circuitry 96 may also be configured to communicate with another computing device via wireless communication techniques, or direct communication through a wired connection. In some examples, telemetry circuitry 96 may be substantially similar to telemetry circuitry 58 of IMD 16 described above, providing wireless communication via an RF or proximal inductive medium. In some examples, telemetry circuitry 96 may include an antenna, which may take on a variety of forms, such as an internal or external antenna.

Examples of local wireless communication techniques that may be employed to facilitate communication between external device 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 98 delivers operating power to the components of programmer 24. Power source 98 may include a battery and a power generation circuit to produce the operating power. In some examples, the battery may be rechargeable to allow extended operation.

Figure 4:
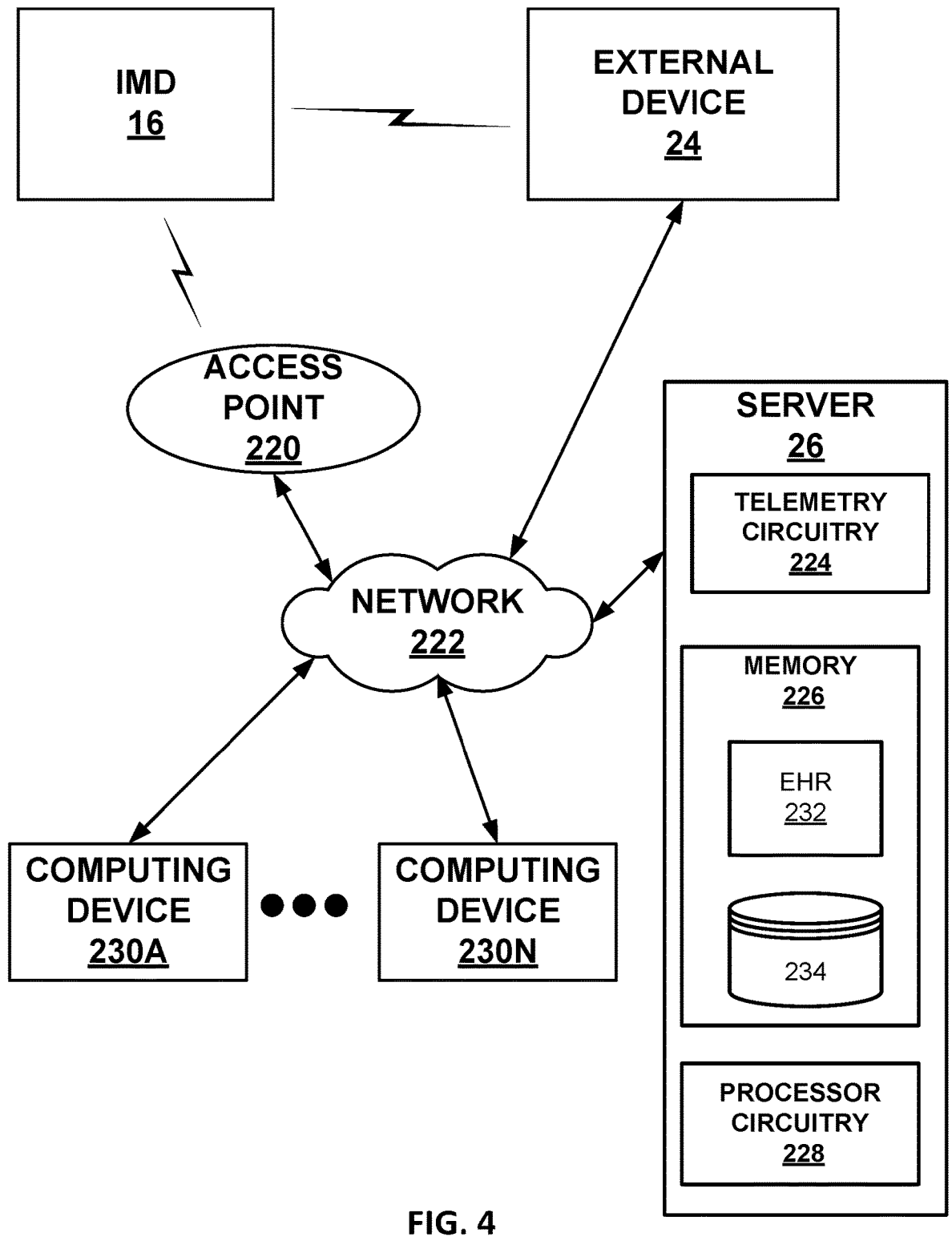
FIG. 4 is a block diagram of an example system that may be configured to perform techniques of the present disclosure.

FIG. 4 is a functional block diagram illustrating an example system that includes external computing devices, such as a server 26 and one or more other computing devices 230A-230N, that are coupled to IMD 16 and external device 24 via a network 222. In this example, IMB 16 may use its telemetry circuitry 58 to, e.g., at different times and/or in different locations or settings, communicate with external device 24 via a first wireless connection, and to communication with an access point 220 via a second wireless connection. In the example of FIG. 4, access point 220, external device 24, server 26, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 16, e.g., periodically or in response to a command from patient 14 or network 222, to retrieve physiological signals acquired by sensor 22. Access point 220 may provide the retrieved data to server 26 via network 222.

In some cases, server 26 may be configured to provide a secure storage site for data that has been captured from IMD 16 and/or external device 24. In some cases, server 26 may assemble data in web pages or other documents for viewing by trained professionals, such as clinicians, via computing devices 230A-230N. The illustrated system of FIG. 4 may be implemented, in some aspects, with general network technology and functionality similar to that provided by the Medtronic CareLink® Network developed by Medtronic plc, of Dublin, Ireland.

This disclosure describes techniques with respect to processor circuitry. While examples may be described with respect to processor circuitry 53 of IMD 16, processor circuitry 90 of external device 24 and processor circuitry 228 of server 26, the techniques of this disclosure may be performed by any one or more of processor circuitry of IMD 16, external device 24, server 26, access point 220 or any of computer devices 230A-230N. In some examples, the techniques of this disclosure may be performed in a distributed manner, with one of more technique performed by processor circuitry of IMD 16, external device 24, server 26, access point 220 or any of computer devices 230A-230N and one or more technique being performed by processor circuitry one or more of IMD 16, external device 24, server 26, access point 220 or any of computer devices 230A-230N. For example, in some examples, processor circuitry 53 of IMB 16 may determine the initial program settings and cause IMB 16 to deliver therapy based on the initial stimulation program settings. In some examples, processor circuitry 228 of server 26 may determine the initial program settings and cause IMD 16 to deliver therapy based on the initial stimulation program settings. In other examples, processor circuitry of a computing device, such as external device 24 or any of computing devices 230A-230N, may determine the initial program settings and cause IMD 16 to deliver therapy based on the initial stimulation program settings. In other examples, any combination of IMD 16, external device 24, server 26 or any of computing devices 230A-230N may determine the initial program settings and cause IMD 16 to deliver therapy based on the initial stimulation program settings.

In the example of FIG. 4, server 26 includes a memory 226 to store information related to a patient and population-informed information. In some examples, the information related to a patient may be stored in an electronic healthcare record (EHR) 232 in memory 226. In some examples, the population-informed information may be stored in a database 234 in memory 226. In some examples, electronic healthcare record 232 may be external to database 234 as shown. In other examples, electronic healthcare record 232 may be in database 234. The population-informed information may include anonymized data relating to other patients. In some examples, the information related to patient 14 or the population-informed information may be stored elsewhere.

Figure 5:
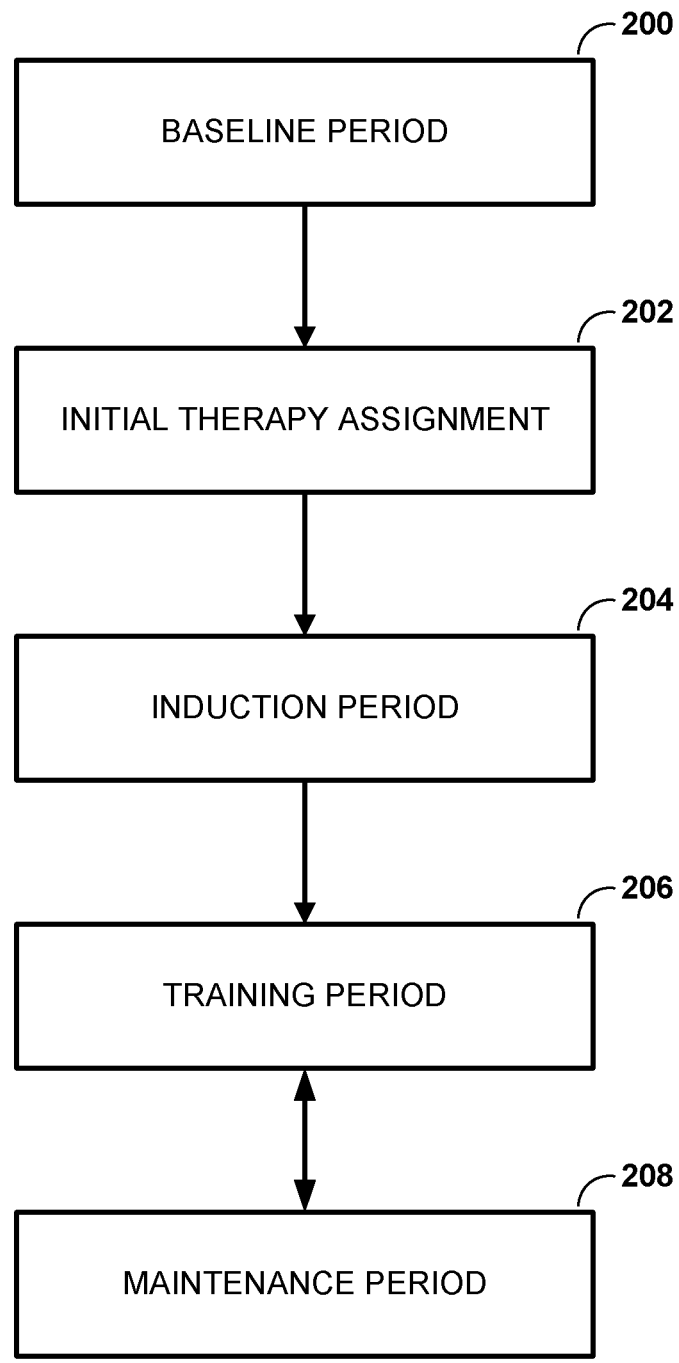
FIG. 5 is a conceptual state diagram of periods of a patient management lifecycle according to the techniques of the present disclosure.

FIG. 5 is a conceptual state diagram illustrating periods of a patient therapy lifecycle. FIG. 5 shows five states: a baseline period 200, an initial therapy assignment 202, an induction period 204, a training period 206 and a maintenance period 208. During baseline period 200, before the patient has been exposed to neuromodulation, such as sacral or tibial neuromodulation, the patient or healthcare provider may digitally enter first information on, for example, external device 24. First information may include basic demographic information and the patient's medical history. For example, a patient or healthcare provider may enter gender, age, BMI, diagnosis, comorbidities, medications, and other information on external device 24. In some examples, external device 24 may collect the first information by posing a number of questions to a patient or healthcare provide on external device 24. In some examples, external device 24 may present the patient or healthcare provider with an electronic form to fill out in order to collect the first information. In this manner, external device 24 may collect the first information by providing the patient or healthcare provider with a direct interface to electronic healthcare record 232. The first information may also include baseline symptom data. As discussed above, baseline symptom data may include indications, symptoms of a disease that the patient is experiencing or physiological parameters. In some examples, the patient may provide baseline symptom data during a minimum number of days to external device 24. The minimum number of days may be in a range of 3-14 days, in some examples. External device 24 may collect the baseline symptom data by posing questions digitally related to the patient's disease symptoms (e.g., urgency, leaks, voids, etc.) as well as questions related to the patient's medications, lifestyle and quality of life including, sleep, fluid intake, food choices, activities of daily living, level of activity, exercise, pain, etc.

In some examples, the first information may also include sensor data. For example, the patient may wear wearable sensors, such as wearable sensor 15, or other sensors to collect more objective data related to sleep and activity. For example, a heart rate sensor, accelerometer, wetness sensor, electromyography sensor or other sensors may be utilized to collect data on disease symptoms or other patient data. External device 24 may collect the sensor data from the wearable sensors.

Telemetry circuitry 96 of external device 24 may provide the captured first information to server 26. In some examples, processor circuitry 228 of server 26 determine whether patient 14 is a candidate for neurostimulation based on the first information. For example, processor circuitry 228 may compare the first information of the patient to first information of other patients in the population-informed information in the database 234 in memory 226 and determine whether other patients with similar first information were successfully treated as they moved along the care pathway from baseline to trial to implant. If other patients with similar first information to the patient have been successfully treated with neurostimulation, that may mean the patient may be a good candidate for neurostimulation. The techniques are described with respect to processor circuitry 228 for ease; however, it should be understood that the processor circuitry that performs the example techniques may be distributed across one or more computing devices 230A-230N and server 26. In this manner, server 26 may utilize the first information as a tool for patient selection. Server 26 may utilize first information to determine a recommended therapy approach including an implant target, initial programming characteristics and behavioral recommendations. For example, processor circuitry 228 may determine a recommended therapy approach based on the patient's diagnosis and indication. For example, processor circuitry 228 may recommended for an overactive bladder patient that their stimulation be cycled once or twice an hour while processing circuitry 228 may recommend for a fecal incontinence patient that their stimulation be cycled once or twice a day.

Once the patient has received a neuromodulation system (either full implant or trial system), the patient may enter initial therapy assignment 202. During initial therapy assignment 202 data from three sources may be captured (by external device 24 or IMD 16, e.g.) and processed, e.g., by server 24, to determine initial stimulation program settings. These three sources may include, for example, the first information captured during the baseline period, second information including physiological data relating to motor and sensory testing which may be performed during the implant procedure, and population-informed data gathered from other patients with similar profiles to the patient. For example, during the implant or post implant in-clinic programming, a series of simple tests to determine motor and sensory thresholds may be collected. Typically, motor threshold information is collected during the implant procedure and sensory threshold information is collected post-op in-clinic as the patient can report when they feel stimulation. The second information may also include the location of the motor and sensory information (e.g., where on the patient's body the sensation was felt or visualized). Additionally, the second information may include electromyography (EMG) data, such as the amplitude, shape and location of an EMG signal collected during implantation.

In some examples, the population-informed data may be anonymized data stored in a database 234 on server 26 or accessible by server 26. For example, server 26 may determine different initial stimulation program settings for patients with a particular disease, e.g., fecal incontinence, with than patients with a different indication, e.g., urinary incontinence patients. These differences may be based on population-informed data, patient specific data or both. Server 26 may determine different initial stimulation program settings for patients with more severe symptoms than patients with less severe symptoms. For patients affected mostly by nocturia during sleep, server 26 may determine initial stimulation program that include only providing therapy only during sleep or providing more therapy during sleep. In some examples, the initial therapy program settings may include more than one stimulation program, in case, for example, the initial program used does not provide symptom relief.

After initial therapy assignment 202 is induction period 204. During induction period 204 (which may exist during the trialing period or post-implant), the initial stimulation program settings may be tested for a minimum number of days. In the case of a trial (pre-implant), this minimum number of days may be in the order of two to four days. In the case of post-implant, this minimum number may be in the order of two to four weeks or more. The number of days of induction period 204 may be defined based on symptom change or defined by a physician or healthcare provider, for example, when a check-in is desired. Induction period 204 may also be adjusted based on the population-informed information. For example, processor circuitry 228 of server 26 may determine that another patient with the same or similar demographics, medical history, activity level, symptoms, disease, disease state or other characteristics had an induction period of a certain length and adjust the induction period length to be closer to or match the induction period length for patient 14 to the induction period length of the other patient. During induction period 204, processor circuitry 228 of server 26 may continue to integrate data (e.g., from healthcare provider, patient input on external device 24, sensors, IMD 16). In some examples, the data captured is similar to the first information captured during the baseline period. For example, external device 24 may provide patient 14 or a healthcare provider with a set of questions to be answered to evaluate the performance of the therapy so far. For example, external device 24 may prompt patient 14 to answer questions regarding symptoms or the efficacy of treatment. Processor circuitry 228 of server 26 may analyze the performance and determine whether to provide a recommendation to modify or maintain the initial stimulation program settings. For example, if the therapy has not impacted symptoms for the patient, processor circuitry 228 of server 26 may suggest switching programs or performing a quick test of the patient's sensory threshold to make adjustments to the amplitude level, or other parameters, of the initial stimulation program settings.

Induction period 204 is followed by training period 206. Training period 206 may last between a few days (during trialing) to a few weeks or even a few months (post-implant), for example. During training period 206, processor circuitry 228 of server 26 attempts to determine the best therapy program or schedule of therapy programs (the maintenance stimulation program settings). Processor circuitry 228 may determine the maintenance stimulation program settings over a period of time. The length of time of the training period may be defined by a physician or healthcare provider. During training period 206, in some examples, less data may be captured from the patient than during earlier periods. In some examples, patient 14 may be able to continue to provide some data through external device 24 relating to patient 14's most bothersome symptoms, how they feel, etc. Processor circuitry 228 may determine, based on the initial stimulation program settings, some personalization and refining of the initial stimulation program settings. The length of training period 206 may be expanded or contracted based on the therapy efficacy and patient 14's satisfaction with the therapy.

In addition, if the therapy is not as effective, a self-reprogramming session may be triggered. The self-reprogramming session may include tests similar to what is typically performed during programming in a clinic with a clinician, where various configurations are programmed, and the stimulation increases until the patient feels a sensation and indicates that they feel a sensation, for example, by pushing a button on external device 24. For example, server 26 may communicate to external device 24 that the self-reprogramming session should occur. Server 26, through external device 24, may guide patient 14 through a series of steps to perform the tests of the self-reprogramming session. External device 24 may communicate with IMD 16 to initiate the self-reprogramming session. During the self-reprogramming session, IMD 16 may utilize different stimulation programs and electrode configurations over the course of time and external device 24 may capture self-reprogramming session information from patient 14, IMD 16 and/or sensors. Example tests may include providing stimulation with: 1) an electrode configuration at a higher amplitude than the initial stimulation program settings; 2) the same electrode configuration at a lower amplitude than the initial stimulation program settings; 3) the same electrode configuration at a higher frequency than the initial stimulation program settings; 4) the same electrode configuration with a different pulse width; 5) the same electrode configuration with different on/off periods than the initial stimulation program settings; and 6) any combination of electrode configurations. Server 26, through external device 24, may pose questions to patient 14 relating to patient 14's symptom relief or comfort during these tests and capture responses from patient 14. During the training period, external device 24 or IMD 16 may capture third information relating to patient 14. The third information relating to patient 14 may include information indicative of the efficacy of the initial stimulation program settings and may include data from the self-reprogramming test. The third information may include data entered by patient 14 on external device 24 or sensor data, such as data from wearable sensor 15 or sensor 22.

Once training period 206 has been completed, maintenance period 208 begins. During maintenance period 208, patient 14 may be able to switch programs and adjust amplitude of the stimulation signal, e.g., by interacting with external device 24. External device 24 may also automatically prompt patient 14 to make changes based on patient 14's provided and recorded data such as symptoms, level of activity and quality of sleep, etc. Settings within each program may be varied and new programs may be created or may be rotated over time based on the patient's status and data captured over time. However, in maintenance period 208, the interaction with server 26 may be minimized as the optimal therapy may have been determined during training period 206. In many cases, patient 14 may not need to change or adjust settings. In some examples, if the therapy efficacy or satisfaction is reduced, user interface 94 of external device 24 may provide simple "turn knobs" labeled as more intuitively as "intensity", "volume" or "amount" that patient 14 may adjust. In some examples, patient 14 may use external device 24 to move back to training period 206, for example, if patient 14 feels that therapy efficacy or patient satisfaction are not acceptable. In some examples, a physician or healthcare provider may also suggest moving back to training period 206 if therapy efficacy and patient satisfaction are not acceptable.

Figure 6:
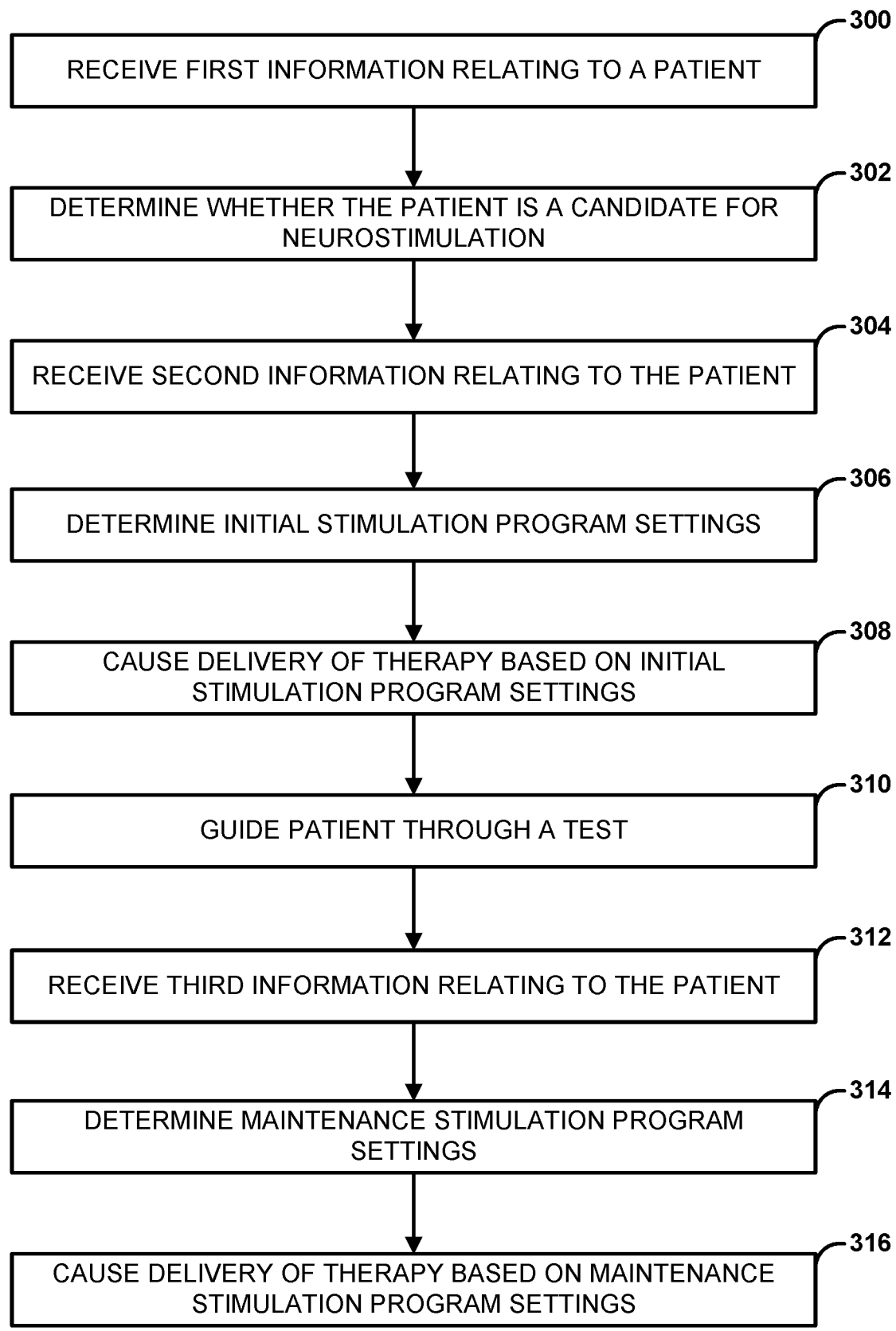
FIG. 6 is a flow diagram illustrating example techniques of the present disclosure.

FIG. 6 is a flow diagram illustrating example techniques according to the present disclosure. The techniques of FIG. 6 may be implemented on server 26, external device 24, IMD 16, computing devices 230A-230N, or any combination thereof. For simplicity purposes, the discussion of the example of FIG. 6 focuses on server 26.

Server 26 may receive first information relating to patient 14 through telemetry circuitry 224 from, e.g., external device 24 through network 222 (300). The first information relating to patient 14 may be captured by, for example, external device 24 during a baseline period that is prior to patient 14 receiving stimulation. The first information relating to patient 14 may include, for example, basic demographic information, patient 14's medical history or basic symptom data. In some examples, the first information includes at least one of symptom data captured over a predetermined time period, medical history data, demographic data, lifestyle data, quality of life data, or sensor data.

Server 26 may store the first information relating to patient 14 in an electronic healthcare record 232 in memory 226. In some examples, processor circuitry 228 of server 26 may determine whether patient 14 is a candidate for neurostimulation based on the first information (302). For example, processor circuitry 228 may compare the first information of the patient to first information of other patients in the population-informed information in the database 234 in memory 226 and determine whether other patients with similar first information were successfully treated as they moved along the care pathway from baseline to trial to implant. If other patients with similar first information to the patient have been successfully treated with neurostimulation, that may mean the patient may be a good candidate for neurostimulation.

Server 26 may receive second information relating to patient 14 through telemetry circuitry 224 from, e.g., external device 24 through network 222 (304). The second information relating to patient 14 may be captured by, for example, external device 24 or IMD 16 during an initial therapy assignment or during clinician testing prior to the initial therapy assignment and may include testing data generated by delivering stimulation during an implant procedure. Server 26 may store the second information relating to patient 14 in the electronic healthcare record 232 in memory 226.

Processor circuitry 228 of server 26 may determine initial stimulation program settings based on the first information relating to patient 14, the second information relating to patient 14 and population-informed information (306). For example, processor circuitry 228 may determine that patient 14's demographics, medical history, activity level, symptoms, disease and disease state most closely match another patient and set the initial stimulation program settings to be based on the current stimulation program settings of the closest matching other patient. The initial stimulation program settings may include stimulation program(s), stimulation parameters (such as a current or voltage amplitude of the stimulation signal, a frequency or pulse rate of the stimulation signal, the shape of the stimulation signal waveform, a duty cycle of the stimulation signal, a pulse width of the stimulation signal, a duty cycle of the stimulation ON/OFF periods, etc.) and/or the combination of electrodes and respective polarities of the electrodes used to deliver the stimulation. The population-informed information may include anonymized data relating to other patients. The population-informed information may be stored in a database 234 in memory 226, for example. Telemetry circuitry 224 of server 26 may provide the initial stimulation program settings to external device 24 or to IMD 16 through network 222, for example. In the case where the initial stimulation program settings are provided to external device 24, telemetry circuitry 96 of external device 24 may provide the initial stimulation program settings to IMD 16. IMD may deliver therapy to patient 14 based on the initial stimulation program settings. In this manner, server 26 may cause, during an induction period, delivery of therapy to patient 14 based on the initial stimulation program settings (308).

In some examples, server 26, during a training period, may communicate with external device 24 to guide patient 14 through a test of at least one of a stimulation program, stimulation parameters or electrode configurations (310). For example, server 26 may cause external device 24 to initiate a self-reprogramming session (a series of tests discussed above) of IMD 16 and capture patient feedback on the self-reprogramming session.

Server 26 may receive third information relating to patient 14 through telemetry circuitry 224 from, e.g., external device 24 through network 222 (312). The third information relating to patient 14 may be captured by, for example, external device 24 or IMD 16 during a training period and be indicative of efficacy of the initial stimulation program settings. For example, patient 14 may input third information on external device 24 or sensor 22 of IMD 16 may sense third information. Server 26 may store the third information relating to patient 14 in the electronic healthcare record 232 in memory 226.

Processor circuitry 228 of server 26 may determine maintenance stimulation program settings based on the third information relating to patient 14 (314). The maintenance stimulation program settings may include stimulation program(s), stimulation parameters (such as a current or voltage amplitude of the stimulation signal, a frequency or pulse rate of the stimulation signal, the shape of the stimulation signal waveform, a duty cycle of the stimulation signal, a pulse width of the stimulation signal, a duty cycle of the stimulation ON/OFF periods, etc.) and/or the combination of electrodes and respective polarities of the electrodes used to deliver the stimulation. The maintenance stimulation program settings may include ranges for each parameter. Sensor data or patient input may be used to ramp up and down the parameters within their ranges or on and off for periods of time.

In some examples, the maintenance stimulation program settings may include more than one therapy program. For example, processor circuitry 228 may determine that the initial stimulation program settings were therapeutic and set the initial program settings as the maintenance stimulation program settings. For example, processor circuitry 228 may determine that the initial stimulation program settings were not therapeutic or were uncomfortable to patient 14 and may determine the maintenance stimulation program settings as settings that, one or more of which, are different than the initial stimulation program settings. In some examples, processor circuitry 228 may use population-informed data to determine the maintenance stimulation program settings. For example, if another patient had a similar initial stimulation program setting as patient 14 and experienced similar efficacy to patient 14 and are now in a maintenance period with the same disease as patient 14, processor 228 may base the maintenance stimulation program settings for patient 14 on the maintenance stimulation program settings for the other patient.

Telemetry circuitry 224 of server 26 may provide the maintenance stimulation program settings to external device 24 or to IMD 16 through network 222, for example. In the case where the maintenance stimulation program settings are provided to external device 24, telemetry circuitry 96 of external device 24 may provide the maintenance stimulation program settings to IMD 16. IMD may deliver therapy to patient 14 based on the maintenance stimulation program settings. In this manner, server 26 may cause, during a maintenance period, delivery of therapy to patient 14 based on the maintenance stimulation program settings (316).

Figure 7:
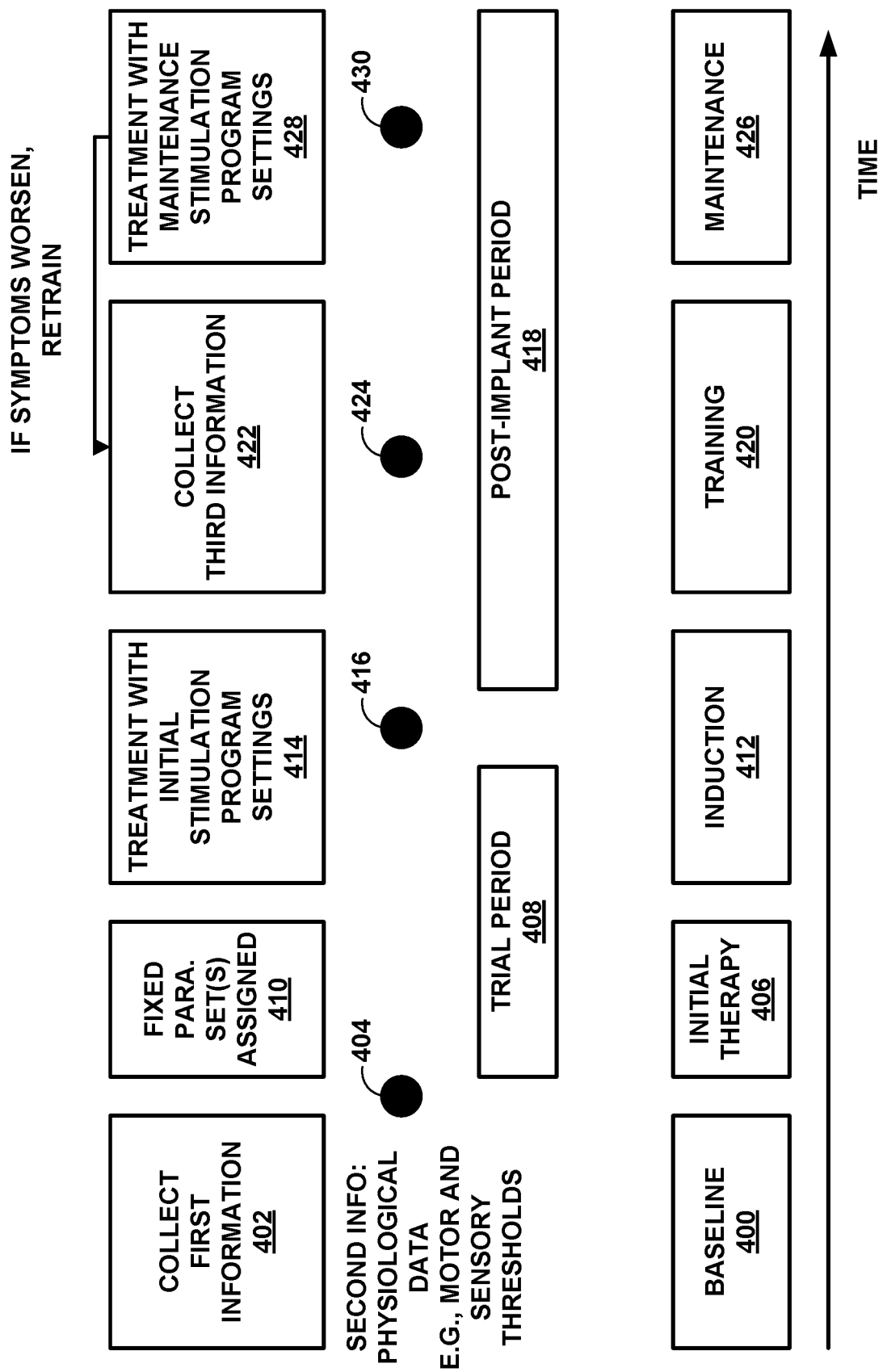
FIG. 7 is a conceptual diagram illustrating example techniques of the present disclosure.

FIG. 7 is a conceptual diagram illustrating a timeline with example techniques of the present disclosure. The techniques of FIG. 7 may be implemented on server 26, external device 24, IMD 16, computing devices 230A-230N, or any combination thereof. For simplicity purposes, the discussion of the example of FIG. 7 focuses on server 26. While the periods (400, 406, 412, 420 and 426) shown in FIG. 7 are shown separated from each other by a period of time, the periods (400, 406, 412, 420 and 426) may, in some examples, be back-to-back such that no time exists between one period and the next. For example, training period 420 may transition to maintenance period 426 without time therebetween.

During baseline period 400, server 26 may receive first information relating to the patient 402 as discussed with respect to FIG. 6. First information relating to the patient 402 may include basic demographic information, indications, physiological parameters, symptoms, medical history, lifestyle data, quality of life data, and sensor data. Server 26 may store the first information relating to the patient 402, e.g., in an electronic healthcare record 232 in memory 226. Before initial therapy assignment 406, a server 26 may receive physiological data 404 (which may be second information related to the patient), such as motor and sensory thresholds of the patient, the location of the motor and sensory information, and EMG signal data. For example, a clinician may conduct testing of the patient to determine motor and sensory thresholds and provide physiological data 404 to server 26, through, e.g., external device 24 over network 222. Server 26 may store physiological data 404 in patient 10's electronic healthcare record 232 in memory 226.

Server 26 may determine a number of initial stimulation program settings which may include fixed parameter sets 410 based on first information 402, physiological data 404 (which may be second information) and population-informed information and provide the fixed parameter sets 410 to IMD 16 or to external device 24 (which may provide the parameter sets to IMD 16), e.g., over network 222 as discussed with respect to FIG. 6. In the example of FIG. 7, initial therapy assignment 406 may begin when a trial period 408 begins.

In the example of FIG. 7, induction period 412 may overlap with trial period 408 and post-implant period 418. IMD 16 may provide therapy to patient 10 during induction period 412 based on the initial stimulation program settings. During induction period 412 there may be minimal changes to the parameters. In the example of FIG. 7, during the implant procedure, a clinician may determine physiological data 416 which may include motor and sensory thresholds, the location of the motor and sensory information, and EMG data. The clinician may provide physiological data 416 to server 26, through, e.g., external device 24 over network 222. Server 26 may store physiological data 416 in patient 10's electronic healthcare record 232 in memory 226.

Induction period 412 may be followed by training period 420. During training period 420, third information 422 may be collected by IMD 16 or external device 24 which may include data related to the patient's symptoms when treated with neurostimulation of various parameters and sensor data. For example, server 26, may communicate with external device 24 to guide patient 14 through a test of at least one of a stimulation program, stimulation parameters or electrode configurations as discussed above or to prompt patient 14 to answer questions regarding patient 14's symptoms or the efficacy of treatment. IMD 16 or external device 24 may collect third information 422. IMD 16 or external device 24 may transmit third information 422 to server 26, e.g., through network 222. Server 26 may store third information 422 in patient 10's electronic healthcare record 232 in memory 226. During training period 420, a clinician may perform testing on the patient to collect physiological data 424 (which may be second information) which may include motor and sensory thresholds, the location of the motor and sensory information, and EMG data. The clinician may collect physiological data 424 on external device 24 and external device 24 may provide physiological data 424 to server 26, e.g. through network 222. Server 26 may store physiological data 424 in patient 10's electronic healthcare record 232 in memory 228.

Processor circuitry 228 of server 26 may determine a therapy plan 428 that may include maintenance stimulation program settings based on the third information relating to patient 14. Sever 26 may provide the maintenance stimulation program settings to IMD 16 or external device 24 (which may provide the maintenance stimulation program settings to IMD 16), e.g., through network 222. Training period 420 may be followed by maintenance period 426, during which IMD 16 utilizes relatively optimized neurostimulation parameters as compared with the initial stimulation program settings. During maintenance period 426, IMD 16 may automatically change a stimulation program or patient 10 may change the stimulation program, through, e.g., external device 24. During maintenance period 426, a clinician may conduct testing of patient 10 to collect physiological data 430 (which may be second information) on, e.g., external device 24. External device 24 may provide physiological data 430 to server 26, e.g., through network 222 and server 26 may record physiological data 430 in patient 10's electronic healthcare record 232. Should sensor data or patient input on external device 24 provided to server 26 by IMD 16 or external device 24 indicate that patient 10's symptoms are worsening, server 26 may move patient 10 back into training period 420, by, e.g., initiating a self-reprogramming session, as discussed above.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various circuitry and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processor circuitry, as well as any combinations of such components, remote servers, remote client devices, or other devices. The term "processor circuitry" or "processor circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components. For example, any circuitry described herein may include electrical circuitry configured to perform the features attributed to that particular circuitry, such as fixed function processor circuitry, programmable processor circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

This disclosure includes the following non-limiting examples.

Example 1. A system for determining neurostimulation therapy, the system comprising: memory configured to store first information relating to a patient, wherein the first information is captured during a baseline period that is prior to the patient receiving stimulation; and processor circuitry coupled to the memory, the processor circuitry being configured to: receive the first information relating to the patient; receive second information relating to the patient, wherein the second information is captured during an initial therapy assignment and the second information comprises testing data generated by delivering stimulation during an implant procedure; determine initial stimulation program settings based on the first information, the second information and population-informed information, the population-informed information being related to other patients; and cause, during a training period, delivery of therapy based on the initial stimulation program settings.

Example 2. The system of example 1, wherein the processor circuitry is further configured to: receive third information relating to the patient, wherein the third information is captured during the training period, the third information being indicative of efficacy of the initial stimulation program settings; determine, based on the third information, maintenance stimulation program settings; and cause, during a maintenance period, delivery of therapy based on the maintenance stimulation program settings.

Example 3. The system of any combination of examples 1-2, wherein the first information comprises symptom data captured over a predetermined time period.

Example 4. The system of any combination of examples 1-3, wherein the first information comprises medical history data.

Example 5. The system of any combination of examples 1-4, wherein the first information comprises demographic data.

Example 6. The system of any combination of examples 1-5, wherein the first information comprises lifestyle data.

Example 7. The system of any combination of examples 1-6, wherein the first information comprises quality of life data.

Example 8. The system of any combination of examples 1-7, wherein the first information comprises sensor data.

Example 9. The system of any combination of examples 1-8, wherein the processor circuitry is further configured to determine whether the patient is a candidate for neurostimulation based on the first information.

Example 10. The system of any combination of examples 1-9, wherein the population-informed information comprises data relating to treatment of other patients with a disease or characteristics, the patient having a same disease or same characteristics.

Example 11. The system of any combination of examples 1-10, wherein the second information comprises physiological data.

Example 12. The system of any combination of examples 1-11, wherein the processor circuitry is further configured to guide the patient through a test of at least one of a stimulation program, stimulation parameters or electrode configurations during the training period.

Example 13. The system of any combination of examples 1-12, further comprising an implantable medical device (IMD) implanted as part of the implant procedure, wherein to cause delivery of the therapy based on the initial stimulation program setting, the processor circuitry is configured to provide the initial stimulation program setting to the IMD.

Example 14. The system of any combination of examples 1-13, further comprising an IMD implanted as part of the implant procedure, wherein the IMD includes the processor circuitry configured to determine initial stimulation program settings, and the processor circuitry is further configured to cause the IMD to deliver the therapy based on the initial stimulation program settings.

Example 15. The system of any combination of examples 1-14, further comprising a server, wherein the server includes the processor circuitry configured to determine initial stimulation program settings, and the server is further configured to provide the initial stimulation program settings to an IMD implanted as part of the implant procedure.

Example 16. The system of any combination of examples 1-15, further comprising a computing device, wherein the computing device includes the processor circuitry configured to determine initial stimulation program settings, and the computing device is further configured to provide the initial stimulation program settings to an IMD implanted as part of the implant procedure.

Example 17. A method comprising: receiving first information relating to a patient, wherein the first information is captured during a baseline period that is prior to the patient receiving stimulation; receiving second information relating to the patient, wherein the second information is captured during an initial therapy assignment and the second information comprises testing data generated by delivering stimulation during an implant procedure; determining initial stimulation program settings based on the first information, the second information and population-informed information, the population-informed information being related to other patients; and causing, during a training period, delivery of therapy based on the initial stimulation program settings.

Example 18. The method of example 17, further comprising: receiving third information relating to the patient, wherein the third information is captured during the training period, the third information being indicative of the efficacy of the initial stimulation program settings; determining, based on the third information, maintenance stimulation program settings; and causing, during a maintenance period, delivery of therapy based on the maintenance stimulation program settings.

Example 19. The method of any combination of examples 17-18, wherein the first information comprises symptom data over a predetermined time period.

Example 20. The method of any combination of examples 17-19, wherein the first information comprises medical history data.

Example 21. The method of any combination of examples 17-20, wherein the first information comprises demographic data.

Example 22. The method of any combination of examples 17-21, wherein the first information comprises lifestyle data.

Example 23. The method of any combination of examples 17-22, wherein the first information comprises quality of life data.

Example 24. The method of any combination of examples 17-23, wherein the first information comprises sensor data.

Example 25. The method of any combination of examples 17-24, further comprising determining whether the patient is a candidate for neurostimulation based on the first information.

Example 26. The method of any combination of examples 17-25, wherein the population-informed information comprises data relating to treatment of others with a disease or characteristics, the patient having a same disease or characteristics.

Example 27. The method of any combination of examples 17-26, wherein the second information comprises physiological data.

Example 28. The method of any combination of examples 17-27, further comprising guiding the patient through a test of at least one of a stimulation program, stimulation parameters or electrode configurations during the training period.

Example 29. The method of any combination of examples 17-28, further comprising providing the initial stimulation program setting to an IMD.

Example 30. The method of any combination of examples 17-29, wherein the initial stimulation program setting is determined by an IMD.

Example 31. The method of any combination of examples 17-30, wherein the initial stimulation program settings are determined by a server.

Example 32. The method of any combination of examples 17-31, wherein the initial stimulation program settings are determined by a computing device.

Example 33. A non-transitory storage medium computer-readable storage medium encoded with instructions that, when executed, cause processor circuitry of a device to: perform the method of any combination of examples 17-32.

Example 34. An implantable medical device comprising: memory configured to store initial stimulation program settings, wherein the initial stimulation program setting are determined based on first information relating to a patient captured during a baseline period that is prior to the patient receiving stimulation, second information captured during an initial therapy assignment including testing data generated by delivering stimulation during an implant procedure of the IMD, and population-informed information related to other patients; and processor circuitry configured to cause a stimulation generator to deliver therapy based on the initial stimulation program setting during a training period.

Various examples have been described herein. Any combination of the described operations or functions is contemplated. These and other examples are within the scope of the following claims. Based upon the above discussion and illustrations, it is recognized that various modifications and changes may be made to the disclosed examples in a manner that does not require strictly adherence to the examples and applications illustrated and described herein. Such modifications do not depart from the true spirit and scope of various aspects of the disclosure, including aspects set forth in the claims.

What is claimed is:

1. A system for determining neurostimulation therapy, the system comprising:
    memory configured to store first information relating to a patient, wherein the first information is captured during a baseline period that is prior to the patient receiving stimulation; and
    processor circuitry coupled to the memory, the processor circuitry being configured to:
        receive the first information relating to the patient;
        receive second information relating to the patient, wherein the second information is captured during an initial therapy assignment and the second information comprises testing data generated by delivering stimulation during an implant procedure;
        determine initial stimulation program settings based on the first information, the second information and population-informed information, the population-informed information being related to other patients; and
        cause, during a training period, delivery of therapy based on the initial stimulation program settings.

2. The system of claim 1, wherein the processor circuitry is further configured to:
    receive third information relating to the patient, wherein the third information is captured during the training period, the third information being indicative of efficacy of the initial stimulation program settings;
    determine, based on the third information, maintenance stimulation program settings; and
    cause, during a maintenance period, delivery of therapy based on the maintenance stimulation program settings.

3. The system of claim 1, wherein the first information comprises at least one of symptom data captured over a predetermined time period, medical history data, demographic data, lifestyle data, quality of life data, or sensor data.

4. The system of claim 1, wherein the processor circuitry is further configured to determine whether the patient is a candidate for neurostimulation based on the first information.

5. The system of claim 1, wherein the population-informed information comprises data relating to treatment of other patients with a disease or characteristics, the patient having a same disease or same characteristics.

6. The system of claim 1, wherein the second information comprises physiological data.

7. The system of claim 1, wherein the processor circuitry is further configured to guide the patient through a test of at least one of a stimulation program, stimulation parameters or electrode configurations during the training period.

8. The system of claim 1, further comprising an implantable medical device (IMD) implanted as part of the implant procedure, wherein to cause delivery of the therapy based on the initial stimulation program setting, the processor circuitry is configured to provide the initial stimulation program setting to the IMD.

9. The system of claim 1, further comprising an IMD implanted as part of the implant procedure, wherein the IMD includes the processor circuitry configured to determine initial stimulation program settings, and the processor circuitry is further configured to cause the IMD to deliver the therapy based on the initial stimulation program settings.

10. The system of claim 1, further comprising a server, wherein the server includes the processor circuitry configured to determine initial stimulation program settings, and the server is further configured to provide the initial stimulation program settings to an IMD implanted as part of the implant procedure.

11. The system of claim 1, further comprising a computing device, wherein the computing device includes the processor circuitry configured to determine initial stimulation program settings, and the computing device is further configured to provide the initial stimulation program settings to an IMD implanted as part of the implant procedure.

12. A method comprising:
receiving first information relating to a patient, wherein the first information is captured during a baseline period that is prior to the patient receiving stimulation;
receiving second information relating to the patient, wherein the second information is captured during an initial therapy assignment and the second information comprises testing data generated by delivering stimulation during an implant procedure;
determining initial stimulation program settings based on the first information, the second information and population-informed information, the population-informed information being related to other patients; and
causing, during a training period, delivery of therapy based on the initial stimulation program settings.

13. The method of claim 12, further comprising:
receiving third information relating to the patient, wherein the third information is captured during the training period, the third information being indicative of the efficacy of the initial stimulation program settings;
determining, based on the third information, maintenance stimulation program settings; and
causing, during a maintenance period, delivery of therapy based on the maintenance stimulation program settings.

14. The method of claim 12, wherein the first information comprises at least one of symptom data over a predetermined time period, medical history data, demographic data, lifestyle data, quality of life data, or sensor data.

15. The method of claim 12, further comprising determining whether the patient is a candidate for neurostimulation based on the first information.

16. The method of claim 12, wherein the population-informed information comprises data relating to treatment of others with a disease or characteristics, the patient having a same disease or characteristics.

17. The method of claim 12, wherein the second information comprises physiological data.

18. The method of claim 12, further comprising guiding the patient through a test of at least one of a stimulation program, stimulation parameters or electrode configurations during the training period.

19. The method of claim 12, further comprising providing the initial stimulation program setting to an IMD.

20. The method of claim 12, wherein the initial stimulation program setting is determined by an IMD.

21. The method of claim 12, wherein the initial stimulation program settings are determined by a server.

22. The method of claim 12, wherein the initial stimulation program settings are determined by a computing device.

23. A non-transitory storage medium computer-readable storage medium encoded with instructions that, when executed, cause processor circuitry of a device to:
receive the first information relating to the patient;
receive second information relating to the patient, wherein the second information is captured during an initial therapy assignment and the second information comprises testing data generated by delivering stimulation during an implant procedure;
determine initial stimulation program settings based on the first information, the second information and population-informed information, the population-informed information being related to other patients; and
cause, during a training period, delivery of therapy based on the initial stimulation program settings.

* * * * *